US012808004B2

(12) United States Patent
Liu et al.

(10) Patent No.: US 12,808,004 B2
(45) Date of Patent: Nov. 24, 2026

(54) MULTIPLEXED, CRISPR-BASED DIAGNOSTICS OF SARS-CoV-2 IN AUTONOMOUS MICROFLUIDIC DEVICE

(71) Applicant: University of Connecticut, Farmington, CT (US)

(72) Inventors: Changchun Liu, Farmington, CT (US); Kun Yin, Farmington, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 621 days.

(21) Appl. No.: 18/262,667

(22) PCT Filed: Feb. 4, 2022

(86) PCT No.: PCT/US2022/015175

§ 371 (c)(1),
(2) Date: Jul. 24, 2023

(87) PCT Pub. No.: WO2022/170013

PCT Pub. Date: Aug. 11, 2022

(65) Prior Publication Data

US 2024/0084408 A1 Mar. 14, 2024

Related U.S. Application Data

(60) Provisional application No. 63/146,124, filed on Feb. 5, 2021.

(51) Int. Cl.
*C12Q 1/70* (2006.01)
*B01L 3/00* (2006.01)

(52) U.S. Cl.
CPC ........ *C12Q 1/701* (2013.01); *B01L 3/502738* (2013.01); *B01L 2200/0647* (2013.01); *B01L 2200/16* (2013.01); *B01L 2400/06* (2013.01)

(58) Field of Classification Search
CPC ......... B01L 2200/0647; B01L 2200/16; B01L 2400/06; B01L 3/502738; C12Q 1/6883; C12Q 1/701
See application file for complete search history.

(56) References Cited

U.S. PATENT DOCUMENTS 9,470,699 B2 10/2016 Peeters
2019/0321825 A1* 10/2019 Pawell .............. B01L 3/502746
2021/0292824 A1* 9/2021 Zhang ...................... C12N 9/78

FOREIGN PATENT DOCUMENTS

CN 111808991 A 10/2020
WO 2019071051 A1 4/2019
(Continued)

OTHER PUBLICATIONS

International Search Report and Written Opinion for International Application PCT/US2022/015175; International Filing Date: Feb. 4, 2022; Date of Mailing: May 18, 2022; 10 pages.
(Continued)

*Primary Examiner* — Jennifer Wecker
(74) *Attorney, Agent, or Firm* — CANTOR COLBURN LLP

(57) ABSTRACT

Described herein is an autonomous, rapid, sensitive, point-of-care target nucleic acid detection system and method based on CRISPR/Cas system. The system and method allow naked eye visualization of multiple target nucleic acid molecules simultaneously in a biological sample in less than an hour. Use of the system and method for multiplex gene diagnosis of SARS-CoV-2 is exemplified.

20 Claims, 8 Drawing Sheets

Specification includes a Sequence Listing.

(56) References Cited

FOREIGN PATENT DOCUMENTS

| | | | | | |
|---|---|---|---|---|---|
| WO | 2020028729 | A1 | | 2/2020 | |
| WO | WO-2020257356 | A2 | * | 12/2020 | .............. B01L 7/525 |

OTHER PUBLICATIONS

Patchsung, M. et al.; "Clinical validation of a Cas13-based assay for the detection of SARS-CoV-2 RNA"; Nature Biomedical Engineering, vol. 4; 2020; pp. 1140-1149.
Xiong, D. et al.; "Rapid detection of SARS-CoV-2 with CRISPR-Cas12a"; PLoS Biology, vol. 18, Issue No. 12; e3000978; 2020; 12 pages; DOI: https://doi.org/10.1371/journal.pbio.3000978.
Yin, K, et al.; "Autonomous lab-on-paper for multiplexed, CRISPR-based diagnostics of SARS-CoV-2"; Lab on a Chip, vol. 21; 2021; pp. 2730-2737.
Bai, Yan et al.; "Presumed Asymptomatic Carrier Transmission of Covid-19"; JAMA Apr. 14, 2020; vol. 323, No. 14; American Medical Association.
Broughton et al.: "CRISPR-Cas12-based detection of SARS-CoV-2", Nature Biotechnology; vol. 38, Jul. 2020; pp. 870-874.
Caliendo et al.: "A CRISPR Way to Diagnose Infectious Diseases", The New England Journal of Medicine, 2017, vol. 377, No. 17; pp. 1685-1687.
Chen et al.: "CRISPR-Cas12a target binding unleashes indiscriminate single-stranded DNase activity"; Science, vol. 360, Issue 3687, Feb. 15, 2018; pp. 436-439.
Chertow, D. S.: "Next-generation diagnostics with CRISPR. CRISPR-Cas biology promises rapid, accurate, and portable diagnostic tools", Science, vol. 360, Issue 6387, Apr. 27, 2018; pp. 381-382.
Ding et al.: "Ultrasensitive and visual detection of SARS-CoV-2 using all-in-one dual CRISPR-Cas12a assay", Nature communications, 2020, 11:4711; 10 pages.
Ferretti et al.: "Quantifying SARS-CoV-2 transmission suggests epidemic control with digital contact tracing"; Science, vol. 368, 619, eabb6936, May 8, 2020; 8 pages.
Gootenberg et al.: "Multiplexed and portable nucleic acid detection platform with Cas13, Cas12a, and Csm6", Science, vol. 360, Issue 6387, 2018; pp. 439-444.
Gootenberg et al.: "Nucleic acid detection with CRISPR-Cas13a/C2c2"; Science, vol. 356, Issue 6336, 2017; pp. 438-442.
Joung et al.; "Detection of SARS-CoV-2 with Sherlock one-pot testing"; N Engl J Med. 383(15):1492-1494; Oct. 8, 2020.
Lan, Lan et al.: "Positive RT-PCR Test Results in Patients Recovered From Covid-19"; JAMA, vol. 323, No. 15, Apr. 21, 2020; pp. 1502-1503.
Larremore et al.: "Test sensitivity is secondary to frequency and turnaround time for Covid-19 surveillance"; MedRxiv 2020.06.22.20136309; doi: https://doi.org/10.1101/2020.06.22.20136309, Jun. 2020; 25 pages.
Lavezzo, Enrico et al.; "Suppression of a SARS-CoV-2 outbreak in the Italian municipality of Vo"; Nature, 584(7821):425-429; Aug. 20, 2020; 19 pages.
Li et al.: "CRISPR-Cas12a-assisted nucleic acid detection"; Cell Discovery, vol. 4:20, 2018; 4 pages.
Li et al.: "CRISPR/Cas Systems towards Next-Generation Biosensing"; Trends in Biotechnology, vol. 37, Issue 7, 2019; pp. 730-743.
Liu et al.: "Community Transmission of Severe Acute Respiratory Syndrome Coronavirus 2, Shenzhen, China, 2020", Emerging Infectious Diseases, vol. 26, No. 6, Jun. 2020; 4 pages.
Niemz et al.: "Point-of-care nucleic acid testing for infectious diseases"; National Institute of Health; Trends Biotechnology, vol. 29, No. 5, May 2011; pp. 240-250.
Schröder, Imke; "Covid-19: A Risk Assessment Perspective"; ACS Chemical Health & Safety, 2020, 27,160-169.
Tahamtan et al.: "Real-time RT-PCR in Covid-19 detection: issues affecting the results"; Expert Review of Molecular Diagnostics, 2020, vol. 20, No. 5; pp. 453-454.
Thi et al.: "A colorimetric RT-Lamp assay and Lamp-sequencing for detecting SARS-CoV-2 RNA in clinical samples", Science Translational Medicine, 2020, vol. 12, Issue 556, eabc7075; 13 pages.
Vogels et al.: "Analytical sensitivity and efficiency comparisons of SARS-CoV-2 RT-qPCR primer-probe sets"; Nature Microbiology; vol. 5; Oct. 2020; pp. 1299-1305.
Wang et al.: "Cas12aVDet: A CRISPR/Cas 12a-Based Platform for Rapid and Visual Nucleic Acid Detection", Analytical Chemistry, 2019, 91; pp. 12156-12161.
Wang, et al.: "Response to Covid-19 in Taiwan Big Data Analytics, New Technology, and Proactive Testing"; JAMA, vol. 323, No. 14, Apr. 14, 2020; pp. 1341-1342.
Woo et al.: "Sensitive fluorescence detection of SARS-CoV-2 RNA in clinical samples via one-pot isothermal ligation and transcription", Nature Biomedical Engineering, vol. 4, Dec. 2020; pp. 1168-1179.
Wu et al.: "SARS-CoV-2 titers in wastewater are higher than expected from clinically confirmed cases"; medRxiv, 2020.04.05.20051540; doi: https://doi.org/10.1101/2020.04.05.20051540; Apr. 2020; 9 pages.
Xiong, E. et al.: "Simultaneous Dual-Gene Diagnosis of SARS-CoV-2 Based onCRISPR/Cas9-Mediated Lateral Flow Assay", Angew. Chem. Int. Ed., vol. 60, 2021; pp. 5307-5315.
Yin et al.: "Dynamic aqueous multiphase reaction system for one-pot CRISPR-Cas12a based ultrasensitive and quantitative molecular diagnosis", American Chemical Society, Anal Chem. 2020, 92(12); pp. 8561-8568.
Yin et al.: "Synergistically enhanced colorimetric molecular detection using smart cup: a case for instrument-free HPV-associated cancer screening", Theranostics, vol. 9, Issue 9, pp. 2637-2645, 2019; 9 pages.

* cited by examiner

SEQUENCE LISTING

```
<160> NUMBER OF SEQ ID NOS: 9

<210> SEQ ID NO 1
<211> LENGTH: 33
<212> TYPE: DNA
<213> ORGANISM: artificial sequence
<220> FEATURE:
<223> OTHER INFORMATION: primer

<400> SEQUENCE: 1

aggcagcagt aggggaactt ctcctgctag aat                               33


<210> SEQ ID NO 2
<211> LENGTH: 33
<212> TYPE: DNA
<213> ORGANISM: artificial sequence
<220> FEATURE:
<223> OTHER INFORMATION: primer

<400> SEQUENCE: 2

ttggccttta ccagacattt tgctctcaag ctg                               33


<210> SEQ ID NO 3
<211> LENGTH: 42
<212> TYPE: RNA
<213> ORGANISM: artificial sequence
<220> FEATURE:
<223> OTHER INFORMATION: guide RNA

<400> SEQUENCE: 3

uaauuucuac uaaguguaga ucugcugcuu gacagauuga ac                     42


<210> SEQ ID NO 4
<211> LENGTH: 30
<212> TYPE: DNA
<213> ORGANISM: artificial sequence
<220> FEATURE:
<223> OTHER INFORMATION: primer

<400> SEQUENCE: 4

aggtttcaaa ctttacttgc tttacataga                                   30
```

-continued

<210> SEQ ID NO 5
<211> LENGTH: 30
<212> TYPE: DNA
<213> ORGANISM: artificial sequence
<220> FEATURE:
<223> OTHER INFORMATION: primer

<400> SEQUENCE: 5
tcctaggttg aagataaccc acataataag 30

<210> SEQ ID NO 6
<211> LENGTH: 49
<212> TYPE: RNA
<213> ORGANISM: artificial sequence
<220> FEATURE:
<223> OTHER INFORMATION: guide RNA

<400> SEQUENCE: 6
uaauuucuac uaaguguaga ugcagcacca gcuguccaac cugaagaag 49

<210> SEQ ID NO 7
<211> LENGTH: 30
<212> TYPE: DNA
<213> ORGANISM: artificial sequence
<220> FEATURE:
<223> OTHER INFORMATION: primer

<400> SEQUENCE: 7
cgcaacaact cagccatcca catccgagtc 30

<210> SEQ ID NO 8
<211> LENGTH: 30
<212> TYPE: DNA
<213> ORGANISM: artificial sequence
<220> FEATURE:
<223> OTHER INFORMATION: primer

<400> SEQUENCE: 8
tatcacggag gggataagtg gaggagtgtc 30

<210> SEQ ID NO 9
<211> LENGTH: 41
<212> TYPE: RNA
<213> ORGANISM: artificial sequence
<220> FEATURE:
<223> OTHER INFORMATION: guide RNA

<400> SEQUENCE: 9
uaauuucuac uaaguguaga uaauuacuug ggugugaccc u 41

MULTIPLEXED, CRISPR-BASED DIAGNOSTICS OF SARS-CoV-2 IN AUTONOMOUS MICROFLUIDIC DEVICE

CROSS REFERENCE TO RELATED APPLICATIONS

This application is a National Stage application of PCT/US2022/015175, filed Feb. 4, 2022, which claims priority to U.S. Provisional Patent Application No. 63/146,124, filed Feb. 5, 2021, both of which are incorporated by reference in their entirety herein.

STATEMENT REGARDING FEDERALLY SPONSORED RESEARCH & DEVELOPMENT

This invention was made with government support under RO1EB023607, R01CA214072, and R21TW010625 awarded by the National Institutes of Health. The government has certain rights in the invention.

SEQUENCE LISTING

The Instant Application contains a Sequence Listing which has been submitted electronically in ASCII format and is hereby incorporated by reference in its entirety. Said ASCII copy, created on Jul. 14, 2023 is named "UCT0284US2_ST25" and is 1,988 bytes in size. The Sequence Listing does not go beyond the disclosure in the application as filed.

FIELD OF THE DISCLOSURE

Described herein is an autonomous microfluidic chip for detection of multiple target pathogen nucleic acids in clinical samples.

BACKGROUND

Molecular diagnostics is a rapid and reliable technology for viral detection. Among nucleic acid tests, the quantitative reverse transcription polymerase chain reaction (RT-qPCR) is considered the current gold-standard diagnostic for SARS-CoV-2 and has been widely used for screening. The RT-qPCR method typically requires expensive equipment, a well-trained operator, and a long detection time, which is not ideal for high-throughput and point-of-care testing, especially in resource-limited settings. In addition, efficient SARS-CoV-2 surveillance requires frequent testing with a fast turnaround time in order to prevent and control the global pandemic which started in 2020. Additionally, the risk of eliciting false-positive and false-negative results remain a problem when using the RT-PCR test. Therefore, a simple, rapid, reliable sensitive, and cost-effective detection method is still needed.

The CRISPR-Cas detection system combining target nucleic acid pre-amplification and CRISPR-Cas-based signal generation has emerged as a next-generation nucleic acid-based molecular diagnostic technique. However, CRISPR-Cas detection frequently elicits false results, is a lengthy process, and requires sophisticated laboratory equipment and trained personnel, which is not ideal for high-throughput and point-of-care testing, especially in resource-limited settings. There is thus a need for a rapid, cost efficient, and accurate diagnostic test system that is autonomous, portable and can be used for point-of-care testing at a sampling site.

SUMMARY

In an aspect, a pathogen nucleic acid detection system comprises, in fluid communication,

- a recombinase polymerase amplification (RPA) reaction chamber for producing RPA amplification products, comprising reagents for multiplex amplification of one or more target pathogen nucleic acids and optionally a positive/negative control;
- a microfluidic chip comprising a multiplexed detection chamber wherein each detection chamber comprises a cleavable nucleic acid probe and reagents, the reagents comprising a CRISPR/Cas12a enzyme, and a guide RNA (gRNA) specific for one target pathogen nucleic acid of the one or more target pathogen nucleic acids or for the positive/negative control; and
- a valve controlling flow of the RPA amplification products from the RPA reaction chamber to the microfluidic chip,
- wherein, in a closed position, the valve stops the passage of the RPA amplification products to the microfluidic chip, and wherein the valve, in an open position, provides passage of the RPA amplification products to the microfluidic chip to initiate CRISPR/Cas12a non-specific cleavage of the cleavable nucleic acid probe, wherein a detectable signal is generated in the detection chambers when the cleavable nucleic acid probe is cleaved by the CRISPR/Cas12a; and
- wherein the detectable signal indicates the presence of the one or more target pathogen nucleic acids or positive/negative control.

In another aspect, a method for detecting a pathogen in a sample or a set of samples collected from a subject or subjects in the foregoing pathogen nucleic acid detection system comprises

- depositing the sample or set of samples in the RPA reaction chamber of the pathogen nucleic acid detection system,
- amplifying the one or more target pathogen nucleic acids and optionally the positive/negative control in each sample to produce RPA amplification products for each sample,
- opening the valve and passing the RNA amplification products through the valve to the microfluidic chip thus initiating CRISPR/Cas12a nonspecific cleavage of the cleavable nucleic acid probe, and
- detecting the detectable signal generated in the multiplexed detection chamber wherein the detectable signal indicates presence of the target pathogen nucleic acid and presence of the pathogen in the sample.

The system and method can simultaneously detect multiple genes for identification of a pathogen within one hour, while obtaining sensitivity of detection of $10^2$ copies of a pathogen gene per test.

DETAILED DESCRIPTION

Figure 1A:
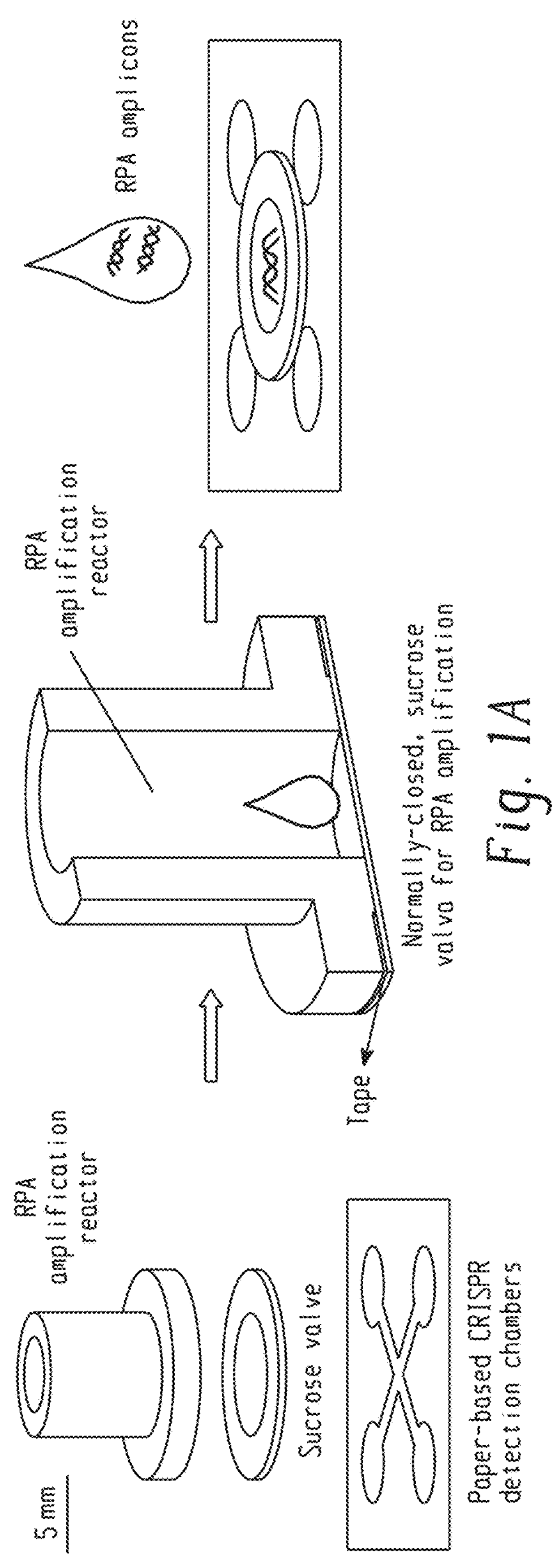
FIG. 1A-D is a scheme of the autonomous lab-on-paper system for multiple, CRISPR-based diagnostics of SARS-CoV-2. 1A is a schematic illustration of the device configuration and working mechanism. A central RPA amplification reactor chamber is fluidically connected through a sucrose valve to multiple peripheral CRISPR detection chambers. The normally-closed, sucrose valve delays the passage of the RPA amplicons for a time sufficient to amplify the target nucleic acids, at which time, the valve dissolves and releases the amplified nucleic acids to the CRISPR detection chambers. 1B illustrates paper-based CRISPR chambers for multiplex gene diagnosis. The CRISPR-Cas12a detection reagents were pre-stored on the CRISPR detection chambers through lyophilization. 1C shows fluorescence image of multiple gene diagnostics of SARS-CoV-2 on the lab-on-paper system. 1D shows photographs of and embodiment the autonomous lab-on-paper system of the present disclosure.

The present disclosure provides diagnostic tests, systems, and methods for rapidly detecting one or more target nucleic acid sequences. Such target nucleic acid sequences may, in some embodiments, be a nucleic acid sequence of a pathogen, such as SARS-CoV-2, an influenza virus, or any other pathogen (e.g., a virus, bacterium, protozoan, prion, viroid, parasite, fungus). The diagnostic tests, systems, and methods described herein utilize methods of isothermal nucleic acid amplification and CRISPR/Cas detection and are capable of producing highly accurate results in relatively short amounts of time (e.g., about 1 hour or less).

The diagnostic tests, systems, and methods described herein are highly sensitive and accurate and may be safely and easily operated or conducted by untrained individuals. As a result, the diagnostic tests, systems, and methods may be useful in a wide variety of contexts. For example, in some cases, the diagnostic tests and systems may be available over the counter for use by consumers. In such cases, untrained consumers may be able to self-administer the diagnostic test (or administer the test to friends and family members) in their own homes (or any other location of their choosing) without the assistance of another person. In some cases, the diagnostic tests, systems, or methods may be operated or performed by employees or volunteers of an organization (e.g., a school, a medical office, a business). For example, a school (e.g., an elementary school, a high school, a university) may test its students, teachers, and/or administrators, a medical office (e.g., a doctor's office, a dentist's office) may test its patients, or a business may test its employees for a particular disease. In each case, the diagnostic tests, systems, or methods may be operated or performed by the test subjects (e.g., students, teachers, patients, employees) or by designated individuals (e.g., a school nurse, a teacher, a school administrator, a receptionist). Point-of-care administration is also contemplated herein, where the diagnostic tests, systems, or methods are administered by a trained medical professional in a point-of-care setting. Certain embodiments additionally contemplate a downloadable software component or software ecosystem, which may assist with test result readout and data aggregation.

In some embodiments, each component of a diagnostic test or system described herein is relatively small Thus, unlike diagnostic systems that require bulky and expensive laboratory equipment (e.g., thermocyclers for PCR tests), diagnostic tests and systems described herein may be easily transported and/or easily stored in homes and businesses. Since expensive laboratory equipment can be avoided, the diagnostic tests, systems, and methods of the present disclosure may be more cost effective than conventional diagnostic tests.

The diagnostic test is based on a detection system and method described herein which are exemplified below using a paper/3D-printing hybrid system for the multiplex diagnosis of SARS-CoV-2 based on a state-of-the-art CRISPR/Cas12a detection technique. The system combines the use of isothermal amplification using recombinase polymerase amplification (RPA) and the high specificity of CRISPR/Cas12a, trans-cleavage. A programmable, auto-controlled valve, e.g., a sucrose valve, was designed to be initially closed in order to separate the RPA reaction chamber products and the CRISPR/Cas12a detection chamber reagents for a time sufficient to amplify the target nucleic acids, at which time, the valve opened, e.g., dissolves, and releases the RPA products comprising amplified target nucleic acids which can migrate by capillary action to the multiplexed detection chamber. The CRISPR/Cas12a reagents in the multiplexed detection chamber include a cleavable nucleic acid probe which produces a detectable signal when the one or more target pathogen nucleic acids is present in the sample. As shown in the Examples below, using the system and method described herein the spike (S) gene and N (nucleoprotein) gene of SARS-CoV-2 can be simultaneously detected along with a housekeeping gene, e.g., a human RNAse P gene, as the positive control. The sensitivity of detection reached $10^2$ genome equivalents (GE) per reaction within 40 mins for a clinical sample diagnosis with 100% negative predictive agreement (NPA) and positive predictive agreement (PPA). Most importantly, the detection can be realized on the portable fluorescent microscope and the results can be directly outputted on a smartphone application, for example. This accurate and convenient detection system provides a method for surveillance and control of COVID-19 as well as other infectious diseases, especially in resource-limited settings.

It should be appreciated that while some examples of the rapid diagnostic tests, systems, and methods provided herein are discussed in the context of specific pathogens or diseases (e.g., SARS-CoV-2), the techniques are not so limited and can be used with any pathogen or disease in which nucleic acid molecules characteristic to or indicative of such pathogen or disease may be detected. Therefore, the examples provided herein of the various embodiments are intended for exemplary purposes only.

In one aspect, the diagnostic system provided herein comprises an RPA reaction chamber or reactor with fluidic communication through a valve, e.g., a sucrose valve, to one or more multiplexed detection chambers. In an aspect, the RPA reaction is an isothermal reaction. Thus, in an aspect, the RPA reaction chamber comprises or receives reagents for amplification, e.g., isothermal amplification, of RNA isolated from a sample. Isothermal amplification utilizes a single temperature to amplify RNA or DNA targets eliminating the need for thermal cycling required in a polymerase chain reaction (PCR) amplification. The multiplexed CRISPR detection chamber receives reagents for CRISPR/Cas detection of targeted nucleic acids and/or negative/positive controls The RPA reaction chamber, CRISPR/Cas detection chamber, or both, can be a space, such as a container, receptacle, or other defined volume or space that can prevent and/or inhibit migration of molecules. The chamber can be of any shape and size of a space defined by physical properties such as walls, for example the walls of a well, tube, or a surface droplet which may be impermeable or semipermeable, or as defined by other means such as chemical, diffusion rate limited, electro-magnetic, or light illumination, or any combination thereof that can contain a sample within a defined space.

By "diffusion rate limited" (for example diffusion defined volumes) is meant spaces that are only accessible to certain molecules or reactions because diffusion constraints effectively defining a space or volume as would be the case for two parallel laminar streams where diffusion will limit the migration of a target molecule from one stream to the other.

By "chemical" defined volume or space is meant spaces where only certain target molecules can exist because of their chemical or molecular properties, such as size, where for example gel beads may exclude certain species from entering the beads but not others, such as by surface charge, matrix size or other physical property of the bead that can allow selection of species that may enter the interior of the bead.

By "electro-magnetically" defined volume or space is meant spaces where the electro-magnetic properties of the target molecules or their supports such as charge, or magnetic properties can be used to define certain regions in a space such as capturing magnetic particles within a magnetic field or directly on magnets.

By "optically" defined volume is meant any region of space that may be defined by illuminating it with visible, ultraviolet, infrared, or other wavelengths of light such that only target molecules within the defined space or volume may be labeled. Exemplary discrete volumes or spaces useful in the disclosed methods include droplets (for example, microfluidic droplets and/or emulsion droplets), hydrogel beads or other polymer structures (for example poly-ethylene glycol di-acrylate beads or agarose beads), tissue slides (for example, fixed formalin paraffin embedded tissue slides with particular regions, volumes, or spaces defined by chemical, optical, or physical means), microscope slides with regions defined by depositing reagents in ordered arrays or random patterns, tubes (such as, centrifuge tubes, microcentrifuge tubes, test tubes, cuvettes, conical tubes, and the like), bottles (such as glass bottles, plastic bottles, ceramic bottles, Erlenmeyer flasks, scintillation vials and the like), wells (such as wells in a plate), plates, pipettes, or pipette tips among others.

Therefore, in one aspect, the RPA reaction chamber can be any suitable size and shape for receiving a sample volume of about 0.5 µl to about 10 µl. In one aspect, the RPA reaction chamber as exemplified in FIG. 1 is a hollow cylinder having an inner diameter of about 2 mm to about 10 mm, and having a height of about 2 mm to about 10 mm. The RPA reaction chamber can be fabricated from material having appropriate thermal and mechanical resistance properties for the use herein, including methacrylate, a thermoplastic polymer (e.g., a polystyrene, a polyolefin such as polyethylene or polypropylene) and/or a metal (e.g., aluminum). In some such embodiments, the RPA reaction chamber may be formed by injection molding, an additive manufacturing process (e.g., 3D printing), and/or a subtractive manufacturing process (e.g., laser cutting), stereolithography, hot embossing, micro-machining, and other known methods.

In an aspect, the sample is added to the RPA reaction chamber along with reagents for RPA amplification. In some embodiments, the RPA reaction chamber comprises reagents for cell lysis. The RPA reaction chamber may already contain RPA reagents, either in solution or lyophilized prior to addition of the sample. The RPA reagents can include one or more reverse transcriptases, one or more recombinases, one or more single-stranded DNA-binding proteins (SSB), and one or more strand-displacing polymerase (such as large fragment of *Bacillus subtilis* Pol 1, Bsu), ATP, a crowding agent such as a high molecular polyethylene glycol, deoxynucleotides (dNTPs) for use in reverse transcription and amplification, and forward and reverse primers specific for one or more of the target nucleic acids to be detected. cDNA can be produced prior to RPA or in the same reaction. By including reverse transcriptase in an RPA reaction, the separate step of cDNA preparation is not required. Reverse transcriptases are known in the art, including Transcriptor® (Roche), Sensiscript® (Qiagen), or MuLV® (Applied Biosystems), to name a few. In some embodiments, the concentration of a reverse transcriptase is in a range of from about 0.01 mg/mL to about 0.05 g/mL, about 0.01 mg/mL to about 0.1 mg/mL, about 0.01 mg/mL to about 0.15 mg/mL, about 0.05 mg/mL to about 0.1 mg/mL, about 0.05 mg/mL to about 0.15 mg/mL, or about 0.10 mg/mL to about 0.15 mg/mL.

In one aspect, RPA reagents include a recombinase, such as T4 UvsX, T4 UvsY, from T4-like bacteriophages which form complexes with oligonucleotide primers and pair the primers with their homologous sequences in duplex DNA. In some embodiments, the concentration of a recombinase enzyme is in a range of from about 0.01 mg/mL to about 0.05 mg/mL, about 0.01 mg/mL to about 0.1 mg/mL, about 0.01 mg/mL to about 0.15 mg/mL, about 0.05 mg/mL to about 0.1 mg/mL, about 0.05 mg/mL to about 0.15 mg/mL, or about 0.10 mg/mL to about 0.15 mg/mL.

In some aspects, RPA reagents comprise one or more single-stranded DNA binding proteins. A non-limiting example of a suitable single-stranded DNA binding protein is T4 gp32 protein. SSB protein binds to the displaced DNA strand and stabilizes the resulting D loop. In certain embodiments, the concentration of the single-stranded DNA binding protein is about 0.1 mg/mL to about 0.5 mg/mL, about 0.6 mg/mL to about 1.0 mg/mL.

In some embodiments, the RPA reagents comprise an isothermal DNA polymerase. Instead of melting DNA strands apart at high temperature, isothermal amplification takes advantage of DNA polymerases with high strand displacement activity that can directly unzip the DNA and synthesize complementary strands. The reaction can occur at temperatures from 22° C. to 45° C. and can be optimized at temperatures between 37° C. and 42° C. Such DNA polymerases are known in the art, for example Sau, Bst or Phi29 DNA polymerases, to name a few. In certain embodiments, the concentration of the DNA polymerase is about 0.01 mg/mL to about 0.05 mg/mL, about 0.06 mg/mL to about 0.1 mg/mL.

RPA reagents may include dNTPs and nucleic acid primers used at any concentration appropriate for the reaction, such as including, but not limited to, a concentration of about 100 nM to about 500 nM, 600 nM to about 1 mM, about 2 mM to about 10 mM, about 20 mM to about 100 mM, 200 mM to about 500 mM, or the like.

In some embodiments, the RPA reagents comprise one or more additional components. Non-limiting examples of suitable components include DL-Dithiothreitol, phosphocreatine disodium hydrate, creatine kinase, and adenosine 5'-triphosphate disodium salt.

RPA reagents can be lyophilized and provided as such in the reaction chamber or in the form of a pellet to be added to the reaction chamber. Lyophilized RPA reagents are stable at ambient temperature for at least 6 months. In some aspects, each component of the diagnostic system is shelf stable for a relatively long period of time, and may be stored at room temperature (e.g., 20-25° C.) for at least 1 month, at least 3 months, at least 6 months, at least 9 months, at least 1 year, at least 5 years, at least 10 years.

Design of primers for RPA amplification is known in the art and involves choice of target region, design of primer candidates, and routine experimental screening. Specifically designed primers of about 30-35 based in length can be used for RPA. Optimization of primer concentrations as primers compete for the recombinase proteins and ratios of each may be tested experimentally as primers for one target can suppress the amplification of another target. Such testing is routine in the art. In some embodiments, the primers may be designed by alignment and identification of conserved sequences in a target pathogen (e.g., using Clustal X or a similar program) and then using a software program (e.g., PrimerExplorer). The specificity of different candidate primers and crRNA may be confirmed using a BLAST search of the GenBank nucleotide database. Primers may be synthesized using any method known in the art. For example, in some embodiments, primers may be synthesized by chemical synthesis, genetic engineering techniques, and/or artificial manipulation of isolated segments of nucleic acids.

Examples of primers for Sars-CoV-2 N gene, S gene, and the mammalian housekeeping gene RNAse P are shown in Table 1. The RPA amplification primers presented in Table 1 were designed to incorporate all SARS-CoV-2 variants with a 99% threshold. In some embodiments, at least one RPA forward primer or RPA reverse primer is at least 1 base pair, at least 2 base pairs, at least 3 base pairs, at least 4 base pairs, or at least 5 base pairs longer or shorter than the primers in Table 1. In some embodiments, the forward primer is at least 70%, at least 75%, at least 80%, at least 85%, at least 90%, at least 95%, at least 99%, or 100% identical to SEQ ID Nos: 1, 4, or 7. In some embodiments, the reverse primer is at least 70%, at least 75%, at least 80%, at least 85%, at least 90%, at least 95%, at least 99%, or 100% identical to SEQ ID Nos: 2, 5, or 8. In certain embodiments, the concentration of the one or more forward primers or reverse primer is at least 0.2 uM, at least 0.3 uM, at least 0.4 uM, at least 0.5 uM, up to at least 100 nM to at least 500 nM. In certain embodiments, the concentration of the one or more forward primers is in a range from 0.3 uM to 0.6 uM.

RPA amplification time can vary depending on the starting level of target nucleic acid copies and can be as low as 3-4 minutes up to 20 minutes, preferably 15 minutes, until the level of target nucleic acid amplicons is detectable. Detection of RPA amplicons can be monitored by end point detection following amplification, or in real time (during amplification) and probes may be used depending on the detection strategy. End-point detection techniques are known in the art and include lateral flow assays, agarose gel electrophoresis, colorimetric detection using primers modified with biotin, fluorescence detection, to name a few.

In some aspects, the diagnostic system described herein is configured to detect one or more target pathogen nucleic acids in a sample having a relatively low concentration of the target nucleic acid (e.g., the system has a relatively low limit of detection for the one or more target nucleic acids). In certain embodiments, the diagnostic system is configured to detect a target nucleic acid (e.g., a nucleic acid of SARS-CoV-2, a SARS-CoV-2 variant, an influenza virus, or another pathogen) at a concentration of at least 5 genomic copies per µL, at least 6 genomic copies per µL, at least 7 genomic copies per µL, at least 8 genomic copies per µL, at least 9 genomic copies per µL, at least 10 genomic copies per µL, at least 15 genomic copies per µL, or at least 20 genomic copies per µL. In certain embodiments, the diagnostic system is configured to detect a target nucleic acid at a concentration in a range from 5-6 genomic copies per µL, 5-7 genomic copies per µL, 5-8 genomic copies per µL, 5-9 genomic copies per µL, 5-10 genomic copies per µL, 5-15 genomic copies per µL, 5-20 genomic copies per µL, 8-10 genomic copies per µL, 8-15 genomic copies per µL, 8-20 genomic copies per µL, 10-15 genomic copies per µL, or 10-20 genomic copies per µL.

TABLE 1

RPA PRIMERS AND CAS12A GUIDE RNAS FOR N/S GENE OF SARS-COV-2 AND HUMAN RNASE P GENE

| Target | RPA primers/Cas12a guide RNA | Sequence (5'-3'), SEQ ID NO |
|---|---|---|
| N gene | RPA forward primer | AGGCAGCAGTAGGGGAACTTCTCCTGCTAGAAT, SEQ ID NO: 1 |
| | RPA reverse primer | TTGGCCTTTACCAGACATTTTGCTCTCAAGCTG, SEQ ID NO: 2 |
| | Cas12a guide RNA | UAAUUUCUACUAAGUGUAGAUCUGCUGCUUGA CAGAUUGAAC, SEQ ID NO: 3 |

TABLE 1-continued

RPA PRIMERS AND CAS12A GUIDE RNAS FOR N/S GENE OF SARS-COV-2 AND HUMAN RNASE P GENE

| Target | RPA primers/Cas12a guide RNA | Sequence (5'-3'), SEQ ID NO |
|---|---|---|
| S gene | RPA forward primer | AGGTTTCAAACTTTACTTGCTTTACATAGA, SEQ ID NO: 4 |
| | RPA reverse primer | TCCTAGGTTGAAGATAACCCACATAATAAG, SEQ ID NO: 5 |
| | Cas12a guide RNA | UAAUUUCUACUAAGUGUAGAUGCAGCACCAGCUGUCCAACCUGAAGAAG, SEQ ID NO: 6 |
| Human RNAse P gene | RPA forward primer | CGCAACAACTCAGCCATCCACATCCGAGTC, SEQ ID NO: 7 |
| | RPA reverse primer | TATCACGGAGGGGATAAGTGGAGGAGTGTC, SEQ ID NO: 8 |
| | Cas12a guide RNA | UAAUUUCUACUAAGUGUAGAUAAUUACUUGGGUGUGACCCU, SEQ ID NO: 9 |

The RPA reaction chamber contents, e.g., reagents and amplified nucleic acid population of the sample, are physically separated from the detection chamber and compartmentalized by use of a valve, e.g., a dissolvable paper-based sucrose valve that is normally closed and prevents or delays the RPA products from mixing with the CRISPR/Cas reagents in the detection chambers until the sucrose valve is open, e.g., dissolves. Non-limiting examples of valve materials include cotton, filter paper, cellulose, cellulose-derived materials, gel, polyurethane, polyester, rayon, nylon, microfiber, viscose, and alginate. Non-limiting examples of valve dissolvable materials include sucrose, trehalose, polyvinylpyrrolidone (PVP), and polyethylene glycol (PEG). When the valve dissolves after a specified time, it opens allowing the delivery of the RPA amplicons with minimal intervention. Exemplified below is a sucrose valve programmed to dissolve in about 15 minutes, providing a delay and sufficient incubation time for generating amplicons in the RPA reaction chamber. In an aspect, the paper-based sucrose valve is produced by injecting the paper valve with a sucrose solution on both sides and drying it. Other sugars can be used such as mannose and trehalose, as well as other dissolvable films such as polyvinyl alcohol (PVA). Other passive methods for fluid manipulation technologies in paper-based devices are known, for example coating the channel with paraffin wax, pullulan, inkjet printing a barrier pattern, to name a few. The valve can be pre-programmed to provide the appropriate delay or time required prior to opening and releasing RPA reaction contents by adjusting the concentration of sucrose or other suitable dissolvable element or film applied to the paper valve. The sucrose concentration can be titrated as in shown in the Examples below in order to provide the desired time delay before opening, for example to provide sufficient time for amplification if for example the sample volume is small or the number of target nucleic acids is small.

The valve and RPA reaction chamber may be assembled to prevent leakage using sealing films or tape, for example, using 3M double-sided tape and/or PCR Sealers tape. The valve and multiplexed detection chambers are similarly assembled. Adhesives, one or more screws or other fasteners, and/or one or more interlocking components can be used to seal the compartments together.

Following RPA nucleic acid amplification, aspects include a step of detection, wherein target nucleic acids are detected within the amplified nucleic acid, or amplicons, of the sample. In some embodiments, target nucleic acids may be detected using any suitable methods, including, but not limited to, those described herein.

In one aspect, detection of amplicons is in a CRISPR/Cas detection chamber which may be in fluid communication with the valve and the RPA chamber. In one embodiment, the amplicons are released from the valve onto a lateral flow assay strip and transported via capillary flow to one or more detection chambers containing reagents for detecting a target nucleic acid. When more than one target nucleic acid is to be detected, the detection chamber may be multiplexed. A multiplexed system may comprise multiple flow lines or channels each leading to multiple detection chambers. In some embodiments, the system comprises 2, 3, 4, 5, 6, 7, 8, 9, 10, or more detection chambers and thereby may screen for the presence of 1, 2, 3, 4, 5, 6, 7, 8, 9, 10, or more target nucleic acid sequences. Therefore, in some aspects, the system comprises a central RPA reaction chamber sealed from fluidic communication with a plurality of peripheral detection chambers by a valve, e.g., a sucrose valve. In some aspects, each peripheral chamber comprises CRISPR/Cas detection reagents specific for a target nucleic acid sequence or a positive/negative control nucleic acid. Therefore, in some embodiments, two nucleic acids (e.g., one target and one control) are simultaneously detected (if present in the sample). In some embodiments, three nucleic acids (e.g., two targets and one control) are detected at the same time (if present in the sample). In some embodiments, four nucleic acids (e.g., two targets and two controls) are detected at the same time (if present in the sample). Thus, multiple nucleic acids, including control nucleic acids, may each be detected simultaneously (if present in the same).

In choosing target pathogen nucleic acids, nucleic acid sequences from pathogen genes can be selected from regions known to maximize inclusivity across known strains, and/or minimize cross-reactivity with related pathogens and genomes likely to be present in the sample. For example, the RPA oligonucleotide primers for amplification and ssDNA probes for detection of SARS-CoV-2 nucleocapsid (N) gene exemplified herein were selected from regions of the virus N gene to maximize inclusivity across known SARS-CoV-2 strains and minimize cross-reactivity with related viruses and genomes likely to be present in the sample. Similarly, other oligonucleotide primers and probes can be selected from SARS-CoV-2 N gene as well as other regions of the SARS-CoV-2 genome, e.g., envelope (E) gene, membrane (M) gene, and/or spike (S) gene. In some embodiments, an additional primer/probe set to detect a positive control such as the human RNase P gene (RP) in control samples and clinical specimens is also included.

In one aspect, the detection chambers are paper based and printed on cellulose paper having properties including medium flow and 11 um pore size, for example Whatman® Grade 1 paper. Non-limiting examples of materials include cotton, filter paper, cellulose, cellulose-derived materials, polyurethane, polyester, rayon, nylon, microfiber, viscose, glass fibers, and alginate. Methods for fabricating microfluidic devices on paper are known, such as the process of printing patterns of solid wax on the surface of the paper, creating complete hydrophobic barriers in paper that define hydrophilic channels, fluid reservoirs, and reaction zones. Exemplified below are hydrophilic channels and detection chambers printed using black wax. The CRISPR/Cas detection reagents can be added to the detection chambers and, optionally, lyophilized.

In an aspect, the CRISPR/Cas detection chamber comprise reagents for a Class 2 CRISPR/Cas (Clustered Regularly Interspaced Short Palindromic Repeats/CRISPR-associated proteins) system, such as Cas12a (previously referred as Cpf1, subtype V-A), that is capable of nonspecific cleavage of ssDNA (single-stranded DNA) and RNA which does not require a PAM (protospacer adjacent motif) recognition site, in addition to successful gene editing (cis-cleavage) at a recognized target site (requires PAM recognition). This attribute, known as trans-cleavage or collateral cleavage, is only activated once bound to an activator (ssDNA or dsDNA) that has complementary base-pairing to a crRNA or guide RNA, gRNA. The crRNA for Cas12a does not require tracrRNA. Guide RNA for Cas12a is often referred to as crRNA, even though there is no tracrRNA. By providing gRNA specific for the chosen target pathogen nucleic acid, hybridization of the gRNA with its specific DNA target sequence, activated the trans-cleavage activity of Cas12a, resulting in cleavage of the collateral ssDNA, which can be labeled to generate a detectable signal, for example a fluorescent signal. Other CRISPR/Cas enzymes that possess the trans-cleavage activity can be used in the device including Cas13b (previously referred C2c2, subtype VI), Cas13a, homologs and orthologs of Cas12a, e.g. FnCas12a (from *Francisella novicida*), LbCas12a (from *Lachnospiraceae* bacterium) and AsCas12a (from *Acidaminococcus* sp.), as well as variants of Cas12a and Cas13a/b still capable of trans-cleavage. A "homolog" "f a protein as used herein is a protein of the same species which performs the same or a similar function as the protein it is a homolog of. Homologous proteins may be but need not be structurally related or are only partially structurally related. An "ortholog" of a protein as used herein is a protein of a different species which performs the same or a similar function as the protein it is an ortholog of. Orthologous proteins may but need not be structurally related or are only partially structurally related.

As mentioned above, Cas12a detection of a chosen target nucleic acid and activation of the trans-cleavage activity require a crRNA or guide RNA (gRNA), a small guide molecule that can guide Cas12a to a specific target nucleic acid sequence and activate Cas12a cleavage activity. The "target nucleic acid sequence" refers to a sequence to which a guide sequence is designed to have complementarity, where hybridization between a target sequence and a guide sequence promotes the formation of a CRISPR complex. A target sequence may comprise RNA or DNA polynucleotides. The term "target RNA" or "target DNA" refers to an RNA or DNA polynucleotide being or comprising the target sequence. In other words, the target RNA or DNA may be an RNA or DNA polynucleotide or a part of a RNA or DNA polynucleotide to which a part of the gRNA, i.e., the guide sequence, is designed to have complementarity and to which the effector function mediated by the complex comprising CRISPR effector protein and a gRNA is to be directed.

As used herein, the term "guide sequence," "crRNA," "guide RNA," or "gRNA" refers to a polynucleotide comprising any polynucleotide sequence having sufficient complementarity with a target nucleic acid sequence to hybridize with the target nucleic acid sequence and to direct sequence-specific binding of an RNA-targeting complex comprising the guide sequence and a CRISPR effector protein to the target nucleic acid sequence. In some example embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at novocraft.com), ELAND (Illumina, San Diego, Calif.), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide may be selected to target any target nucleic acid sequence.

In certain embodiments, a crRNA or analogous polynucleotide comprising a guide sequence, is an RNA, a DNA or a mixture of RNA and DNA, and/or wherein the polynucleotide comprises one or more modified nucleotide. As used herein, a 'modified nucleotide' may refer to a nucleotide comprising a base such as, for example, adenine, guanine, cytosine, thymine, and uracil, xanthine, inosine, and queuosine that may have been modified by the replacement or addition of one or more atoms or groups. For example, the modification may comprise a nucleotide that is modified with respect to the base moiety, such as a/an alkylated, halogenated, thiolated, aminated, amidated, or acetylated base, in various combinations. Modified nucleotides also may include nucleotides that comprise a sugar moiety modification (e.g., 2'-fluoro or 2'-O-methyl nucleotides), as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

In certain embodiments, the crRNA or gRNA can comprise any structure, including but not limited to a structure of a native crRNA. The gRNA can comprise a bulge, a hairpin, or a stem loop, preferably a single stem loop. In some embodiments, a gRNA is about or more than about 5, 10, 15, 20, 25, 30, 35, 40, 45, 50, 75, or more nucleotides in length. In some embodiments, a gRNA is less than about 75, 50, 45, 40, 35, 30, 25, 20, 15, 12, or fewer nucleotides in length. Preferably the gRNA is 10 to 30 nucleotides long. The gRNA may be synthesized using any method known in the art. For example, in some embodiments, an artificial gRNA may be synthesized by chemical synthesis, genetic engineering techniques, and/or artificial manipulation of isolated segments of nucleic acids. Exemplary gRNAs for the N gene and S gene of SARS-CoV-2 are shown in Table 1. In some embodiments, the crRNA is at least 70%, at least 75%, at least 80%, at least 85%, at least 90%, at least 95%, at least 99%, or 100% identical to crRNA sequences SEQ ID NOs:3, 6 or 9. In some embodiments, the probe is at least 70%, at least 75%, at least 80%, at least 85%, at least 90%, at least 95%, at least 99%, or 100% identical to SEQ ID Nos:3, 6, or 9. In some embodiments, the concentration of the gRNA is at least 30 nM, at least 40 nM, at least 60 nM, at least 70 nM, at least 80 nM, up to at least 200 nM. In some embodiments, the concentration of the probe is in a range from 40 nM to about 75 nM.

In certain aspects, CRISPR/Cas detection reagents include a cleavable nucleic acid probe. In one embodiment, the cleavable nucleic acid probe is a ssDNA probe. As mentioned above, the gRNA activated CRISPR/Cas12a can nonspecifically trans-cleave a ssDNA probe. In one aspect, the ssDNA probe is labeled with a reporter. In one aspect, the reporter is modified at the 5' end with a fluorescent group. In one aspect, the ssDNA probe is labeled with a quencher at the 3' end. The quencher, when in close proximity to the fluorophore, quenches the fluorescence emitted. The fluorophores and quenchers may be easily chosen for the desired probe application. Different fluorescent dyes have been used to engineer oligonucleotide probes, for example fluorescein (fluorescein isothiocyanate, FITC), TAMRA (red-fluorescent tetramethylrhodamine, sometimes also used as a quencher), Cyanine dyes (CY3, CY5), Texas red (ROX), HEX, JOE, Oregon green, rhodamine 6 G, coumarin, pyrene, and others. Additionally, in fluorescence quenching approaches, quencher molecules, e.g., dimethylaminophenylazobenzoic acid (DABCYL), BHQ1, BHQ2, MGBNFQ, Iowa Black, have been covalently attached to the fluorescent oligonucleotides such that when the ssDNA is cleaved by the CRISPR/Cas enzyme, a detectable signal, fluorescence, is produced that is visible to the naked eye or with the aid of a machine, and indicates that the target gene is present. Other fluorophores and quenchers as well as methods for fluorescent labeling of nucleic acids are known in the art.

In certain embodiments, the nonspecific ssDNA probe can be any oligonucleotide of any length which when cleaved can produce a detectable signal. In some embodiments, the ssDNA probe is a short oligonucleotide of about 2, 3, 4, or 5 nucleotides or more in length. In some embodiments the ssDNA is or comprises the sequence TTATT or is at least 70%, at least 75%, at least 80%, at least 85%, at least 90%, at least 95%, at least 99%, or 100% identical to the sequence. In some embodiments, the concentration of the probe is at least 20 nM, at least 35 nM, at least 50 nM, at least 75 nM, at least 100 nM. In some embodiments, the concentration of the probe is in a range from 30 nM to 60 nM.

Therefore, in one aspect, the diagnostic system is used in a method for detecting a pathogen in a sample or a set of samples collected from a subject or subjects, comprising preparing the sample or set of samples for recombinase polymerase amplification (RPA) of one or more target pathogen nucleic acids in each sample and optionally a positive/negative control. A sample can be from any patient specimen or any body fluid including, but not limited to, urine, sputum, respiratory washes, nasal and other respiratory specimens, cell scrapings from the mouth or interior cheek, exhaled breath particles, blood, plasma, saliva, amniotic fluid, vaginal and anal swabs, culture media (e.g. liquid in which a cell, such as a pathogen cell, has been grown) surgical biopsy specimens, organ tissues (skin, lymphatic nodes, liver, lungs, stomach, kidney), as well as animal and plant products (eggs, shrimps, rice, milk, fruit).

Clinical sample preparation may include cell lysis in order to break open or lyse a cell to release nucleic acids. Cell lysis components can be included in the system and may include, but is not limited to, a detergent, a salt as described above, such as NaCl, KC1, ammonium sulfate, or others. Detergents that may be appropriate for the invention may include Triton X-100, sodium dodecyl sulfate (SDS), CHAPS (3-[(3-cholamidopropyl)dimethylammonio]-1-propanesulfonate), ethyl tri methyl ammonium bromide, nonyl phenoxypolyethoxylethanol (NP-40). Concentrations of detergents may depend on the particular application and may be specific to the reaction in some cases.

Crude extracts of these samples can be used for RPA, and if desired, the detection system can be designed to incorporate a microfluidic device to include steps for plasma separation or nucleic acid isolation.

Sample preparation can include extracting and concentration of the target nucleic acid molecules and removing potential inhibitors of amplification from the extract. Methods for isolation of nucleic acids from biological samples are known.

In some embodiments, one or more reagents of the system further comprise one or more additives that may enhance reagent stability (e.g., protein stability). Non-limiting examples of suitable additives include trehalose, polyethylene glycol (PEG), polyvinyl alcohol (PVA), and glycerol.

Therefore, in one aspect, the diagnostic system is used in a method for detecting a pathogen in a sample or a set of samples collected from a subject or subjects, comprising preparing the sample or set of samples for recombinase polymerase amplification (RPA) of one or more target pathogen nucleic acids in each sample and optionally a positive/negative control; amplifying the one or more target pathogen nucleic acids and optionally a positive/negative control in each sample in an RPA reaction chamber to produce a RPA amplification product for each sample; allowing the RPA amplification product produced from each sample to flow through a sucrose valve to a microfluidic chip, wherein the sucrose valve controls flow of reagents from the RPA reaction chamber to the microfluidic chip, the microfluidic chip comprises a multiplexed detection chamber comprising CRISPR/Cas12a detection reagents wherein each detection chamber comprises a CRISPR/Cas12a enzyme, a guide RNA (gRNA) specific for one target pathogen nucleic acid of the one or more target nucleic acids or for the positive/negative control, and a cleavable nucleic acid probe, wherein when the sucrose valve is opened, RPA amplification product from the RPA reaction chamber flows into the multiplexed detection chambers and initiates CRISPR/Cas12a nonspecific cleavage of the cleavable nucleic acid probe, producing a detectable signal; and detecting the detectable signal in the multiplexed detection chamber wherein presence of a signal in the one or more detection chambers with reagents for a target pathogen nucleic acid of the one or more target pathogen nucleic acids indicates presence of the target pathogen nucleic acid and presence of the pathogen in the sample.

In one aspect, there is simultaneous detection of signal from multiple detection chambers.

In one aspect, the method allows detection of multiple genes or nucleic acids from the same or a different pathogen in a sample by providing CRISPR/Cas reagents into one or more individual detection chambers, the individual reagents comprising a CRISPR/Cas system specific for a chosen pathogen nucleic acid as described herein. In one aspect, a diagnostic device configured to detect a first target nucleic acid (e.g., a nucleic acid of SARS-CoV-2) and a second target nucleic acid (e.g., a nucleic acid of an influenza virus) may comprise a first set of RPA primers and gRNA directed to the first target nucleic acid and a second set of RPA primers and gRNA directed to the second target nucleic acid.

In one aspect, reagents for detecting a positive and/or negative control are prepared along with the reagents for the desired targets. A negative control is a control group that is not expected to produce results, for example, a solution known to be free of the desired targets, exemplified below as a SARS-CoV-2 virus free solution. A positive control is a control group that is known to produce results, for example a solution known to contain the desired target sequence which confirms the correctness of the test. In some aspects, a positive control is also an internal control which is included in the assay for validation, for example a housekeeping gene that regulates basic cellular functions and displays highly uniform expression. Frequently used housekeeping genes in mammalian cells are known in the art and include actin, glyceraldehyde 3-phosphate (GAPDH), ubiquitin, β-tubulin, ribonuclease P RNA component H1, telomerase reverse transcriptase, to name a few.

The failure to detect a positive control may indicate one or more of the following: improper specimen collection resulting in the lack of sufficient sample material in the diagnostic assay, improper extraction of nucleic acids from clinical materials resulting in loss of nucleic acids and/or nucleic acid degradation, improper assay set up and execution, and/or reagent or equipment malfunction.

Successful detection of the positive control indicates successful collection, extraction, amplification, and CRISPR/Cas cleavage activity of nucleic acids from the sample. A positive result on the positive control band indicates that the user successfully obtained the sample material, the lysis and extraction (if applicable) steps were completed effectively, and the CRISPR/Cas cleavage was effective in the sample. In instances where the positive control is detected, the test is valid.

The present method may be used with a wireless lab-on-chip (LOC) diagnostic sensor system (see e.g., U.S. Pat. No. 9,470,699 "Diagnostic radio frequency identification sensors and applications thereof"). In certain aspects, the method is performed in a LOC controlled by a wireless device (e.g., a cell phone, a personal digital assistant (PDA), a tablet) and results are reported to said device.

In certain aspects, the diagnostic system may include handheld portable devices for diagnostic reading of an assay such as a personal phone with applications for personalized healthcare monitoring and management, an mReader from Mobile Assay, or Holomic Rapid Diagnostic Test Reader.

As noted herein, certain embodiments allow detection via colorimetric change which has certain attendant benefits when embodiments are utilized in POC situations and/or in resource poor environments where access to more complex detection equipment to readout the signal may be limited. However, portable embodiments disclosed herein may also be coupled with hand-held spectrophotometers that enable detection of signals outside the visible range, or use of a hand-held UV light, or other suitable device, may be successfully used to detect a signal.

Any of the rapid diagnostic tests described herein may be formulated as a kit. As used herein a "kit" comprises a package or an assembly including one or more of the test compositions of the invention. Any one of the kits provided herein may comprise any number of reaction tubes, wells, chambers, or other vessels. Each of the components of the kit (e.g., reagents) may be provided in liquid form (e.g., in solution). In some cases, one or more reagents described herein (e.g., lysis reagents, nucleic acid amplification reagents, reagents for CRISPR/Cas detection) are in solid form (e.g., lyophilized, dried, crystallized, air jetted). In certain cases, one or more (and, in some cases, all) nucleic acid amplification reagents are in solid form. In some cases, one or more CRISPR/Cas detection reagents are in solid form. In some cases, one or more (and, in some cases, all) lysis reagents are in solid form. In certain embodiments, all reagents of a diagnostic test, system, or method are in solid form. In some embodiments, the one or more reagents in solid form are in the form of one or more beads, pellets, and/or tablets. The one or more beads, pellets, and/or tablets may comprise any reagent or combination of reagents described herein. Therefore, some embodiments that do not require a supporting device are also contemplated, i.e., the system may be applied to any surface or fluid that will support the reactions disclosed herein and allow for detection of a positive detectable signal from that surface or solution. In addition to freeze-drying, the systems may also be stably stored and utilized in a pelletized form. Polymers useful in forming suitable pelletized forms are known in the art. In some embodiments, the one or more beads, pellets, and/or tablets are stable at room temperature for a relatively long period of time. In certain embodiments, the one or more beads and/or tablets are stable at room temperature for about 1 month to about 6 months, about 9 months to about 2 years, or more.

A kit may, in some cases, include instructions in any form that are provided in connection with the compositions of the invention in such a manner that one of ordinary skill in the art would recognize that the instructions are to be associated with the compositions of the invention. The instructions may include instructions for performing any one of the tests provided herein. The instructions may include instructions for the use, modification, mixing, diluting, preserving, administering, assembly, storage, packaging, and/or preparation of the compositions and/or other compositions associated with the kit. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications). In some embodiments, the instructions are provided as part of a software-based application, as described herein. In some embodiments, the kit contains a sterile swab.

As shown in the Examples below, the method and system described herein provides a rapid diagnostic test which produces results in less than 1 hour with high sensitivity, allowing detection of $10^2$ genome copies of pathogen per test, with a specificity of 100%. In some embodiments, the diagnostic system has a relatively high positive percent agreement (PPA) and/or a relatively high negative percent agreement (NPA) with a reference test. In some cases, the diagnostic system may be compared to a reference test by testing a certain number of subjects using both the diagnostic system and the reference test, and positive percent agreement and/or negative percent agreement values may be obtained. Positive percent agreement can be calculated by dividing the number of positive results obtained by the diagnostic system by the number of positive results obtained using the reference test and multiplying by 100. In some embodiments, the diagnostic system has a positive percent agreement with a reference test of at least 90%, at least 91%, at least 92%, at least 93%, at least 94%, at least 95%, at least 96%, at least 97%, at least 98%, at least 99%, or about 100%. In some embodiments, the diagnostic system has a positive percent agreement with a reference test in a range from 90-95%, 90-98%, 90-99%, 90-100%, 95-98%, 95-99%, 95-100%, 98-100%, or 99-100%. Negative percent agreement can be calculated by dividing the number of negative results obtained by the diagnostic system by the number of negative results obtained by the reference test and multiplying by 100. In some embodiments, the diagnostic system has a negative percent agreement with a reference test of at least 90%, at least 91%, at least 92%, at least 93%, at least 94%, at least 95%, at least 96%, at least 97%, at least 98%, at least 99%, or about 100%. In some embodiments, the diagnostic system has a negative percent agreement with a reference test in a range from 90-95%, 90-98%, 90-99%, 90-100%, 95-98%, 95-99%, 95-100%, 98-100%, or 99-100%.

In some embodiments, the total time for performing the diagnostic method is about 100 minutes or less, about 90 minutes or less, about 80 minutes or less, about 75 minutes or less, about 70 minutes or less, about 65 minutes or less, about 60 minutes or less, about 50 minutes or less, 45 minutes or less, about 40 minutes or less, or about 30 minutes or less. In some embodiments, the total time for performing the diagnostic method is in a range from 30 to 40 minutes, 30 to 45 minutes, 30 to 50 minutes, 30 to 60 minutes, 30 to 65 minutes, 30 to 70 minutes, 30 to 75 minutes, 30 to 80 minutes, 30 to 90 minutes, 30 to 100 minutes, 45 to 60 minutes, 45 to 65 minutes, 45 to 70 minutes, 45 to 75 minutes, 45 to 80 minutes, 45 to 90 minutes, 45 to 100 minutes, 60 to 70 minutes, 60 to 75 minutes, 60 to 80 minutes, 60 to 90 minutes, 60 to 100 minutes, 70 to 75 minutes, 70 to 80 minutes, 70 to 90 minutes, 70 to 100 minutes, 75 to 80 minutes, 75 to 90 minutes, 75 to 100 minutes, 80 to 90 minutes, or 80 to 100 minutes.

In some embodiments, the rapid diagnostic tests, systems, and methods of the present disclosure are applied to a subject who is suspected of having a pathogenic infection or disease, but who has not yet been diagnosed as having such an infection or disease. A subject may be "suspected of having" a pathogenic infection or disease when the subject exhibits one or more signs or symptoms of such an infection or disease. Such signs or symptoms are well known in the art and may vary, depending on the nature of the pathogen and the subject. Signs and symptoms of disease may generally include any one or more of the following: fever, chills, cough (e.g., dry cough), generalized fatigue, sore throat, runny nose, nasal congestion, muscle aches, difficulty breathing (shortness of breath), congestion, runny nose, headaches, nausea, vomiting, diarrhea, loss of smell and/or taste, skin lesions (e.g., pox), or loss of appetite. Other signs or symptoms of disease are specifically contemplated herein. As a non-limiting example, symptoms of coronaviruses (e.g., COVID-19) may include, but are not limited to, fever, cough (e.g., dry cough), generalized fatigue, sore throat, runny nose, nasal congestion, muscle aches, loss of smell and/or taste, and difficulty breathing (shortness of breath). As a non-limiting example, symptoms of influenza may include, but are not limited to, fever, chills, muscle aches, cough, sore throat, runny nose, nasal congestion, and generalized fatigue. A subject may also be "suspected of having" a pathogenic infection or disease despite exhibiting no signs or symptoms of such an infection or disease (e.g., the subject is asymptomatic).

In certain example embodiments, the systems, devices, and methods, disclosed herein are directed to detecting the presence of one or more pathogens in a sample, such as a biological sample obtained from a subject. In certain example embodiments, the pathogen may be a bacterium, a fungus, a yeast, a protozoan, a parasite, or a virus. Accordingly, the methods disclosed herein can be adapted for use in other methods (or in combination) with other methods that require quick identification of pathogen species, monitoring the presence of pathogen proteins (antigens), antibodies, antibody genes, detection of certain phenotypes (e.g., bacterial resistance), monitoring of disease progression and/or outbreak, and antibiotic screening. Because of the rapid and sensitive diagnostic capabilities of the embodiments disclosed here, detection of pathogen species type, down to a single nucleotide difference, and the ability to be deployed as a POC device, the embodiments disclosed herein may be used guide therapeutic regimens, such as selection of the appropriate antibiotic or antiviral. The embodiments disclosed herein may also be used to screen environmental samples (air, water, surfaces, food etc.) for the presence of microbial contamination.

The following provides an example list of the types of pathogens or microbes that might be detected using the embodiments disclosed herein. In certain example embodiments, the pathogen is a bacterium. Examples of bacteria that can be detected in accordance with the disclosed methods include without limitation any one or more of (or any combination of) *Acinetobacter baumanii, Actinobacillus* sp., *Actinomycetes, Actinomyces* sp. (such as *Actinomyces israelii* and *Actinomyces naeslundii*), *Aeromonas* sp. (such as *Aeromonas hydrophila, Aeromonas veronii biovar sobria* (*Aeromonas sobria*), and *Aeromonas caviae*), *Anaplasma phagocytophilum, Anaplasma marginale Alcaligenes xylosoxidans, Acinetobacter baumannii, Actinobacillus actinomycetemcomitans, Bacillus* sp. (such as *Bacillus anthracis, Bacillus cereus, Bacillus subtilis, Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae, Bifidobacterium* sp., *Bordetella* sp. (such as *Bordetella pertussis, Bordetella parapertussis*, and *Bordetella bronchiseptica*), *Borrelia* sp. (such as *Borrelia recurrentis*, and *Borrelia burgdorferi*), *Brucella* sp. (such as *Brucella abortus, Brucella canis, Brucella melitensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp. *Coxiella burnetiid, Corynebacterium* sp. (such as, *Corynebacterium diphtheriae, Corynebacterium jeikeium* and *Corynebacterium*), *Clostridium* sp. (such as *Clostridium perfringens, Clostridium difficile, Clostridium botulinum* and *Clostridium tetani*), *Eikenella corrodens, Enterobacter* sp. (such as *Enterobacter aerogenes, Enterobacter agglomerans, Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chaffeensis* and *Ehrlichia canis*), *Epidermophyton floccosum, Erysipelothrix rhusiopathiae, Eubacterium* sp., *Francisella tularensis, Fusobacterium nucleatum, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus, Helicobacter* sp. (such as *Helicobacter pylori, Helicobacter cinaedi* and *Helicobacter fennelliae*), *Kingella kingae, Klebsiella* sp. (such as *Klebsiella pneumoniae, Klebsiella granulomatis* and *Klebsiella oxytoca*), *Lactobacillus* sp., *Listeria monocytogenes, Leptospira interrogans, Legionella pneumophila, Leptospira interrogans, Peptostreptococcus* sp., *Mannheimia haemolytica, Microsporum canis, Moraxella catarrhalis, Morganella* sp., *Mobiluncus* sp., *Micrococcus* sp., *Mycobacterium* sp. (such as *Mycobacterium leprae, Mycobacterium tuberculosis, Mycobacterium paratuberculosis, Mycobacterium intracellulare, Mycobacterium avium, Mycobacterium bovis*, and *Mycobacterium marinum*), *Mycoplasma* sp. (such as *Mycoplasma pneumoniae, Mycoplasma hominis*, and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Pityrosporum orbiculare* (*Malassezia furfur*), *Plesiomonas shigelloides. Prevotella* sp., *Porphyromonas* sp., *Prevotella melaninogenica, Proteus* sp. (such as *Proteus vulgaris* and *Proteus mirabilis*), *Providencia* sp. (such as *Providencia alcalifaciens, Providencia rettgeri* and *Providencia stuartii*), *Pseudomonas aeruginosa, Propionibacterium acnes, Rhodococcus equi, Rickettsia* sp. (such as *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella choleraesuis* and *Salmonella typhimurium*), *Serratia* sp. (such as *Serratia marcescens* and *Serratia liquefaciens*), *Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus haemolyticus, Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equisimilis*, Group D streptococci, *Streptococcus bovis*, Group F streptococci, and *Streptococcus anginosus* Group G streptococci), *Spirillum minus, Streptobacillus moniliformis, Treponema* sp. (such as *Treponema carateum, Treponema pertenue, Treponema pallidum* and *Treponema endemicum, Trichophyton rubrum*, T mentagrophytes, *Tropheryma whippelii, Ureaplasma urealyticum, Veillonella* sp., *Vibrio* sp. (such as *Vibrio cholerae, Vibrio parahaemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metschnikovii, Vibrio damsela* and *Vibrio furnissii*), *Yersinia* sp. (such as *Yersinia enterocolitica, Yersinia pestis*, and *Yersinia pseudotuberculosis*) and *Xanthomonas maltophilia* among others.

Fungi

In certain example embodiments, the pathogen is a fungus or a fungal species. Examples of fungi that can be detected in accordance with the disclosed methods include without limitation any one or more of (or any combination of), *Aspergillus, Blastomyces, Candidiasis, Coccidioidomycosis, Cryptococcus neoformans, Cryptococcus gattii*, sp. *Histoplasma* sp. (such as *Histoplasma capsulatum*), *Pneumocystis* sp. (such as *Pneumocystis jirovecii*), *Stachybotrys* (such as *Stachybotrys chartarum*), *Mucormycosis, Sporothrix*, fungal eye infections ringworm, *Exserohilum, Cladosporium.*

In certain example embodiments, the fungus is a yeast. Examples of yeast that can be detected in accordance with disclosed methods include without limitation one or more of (or any combination of), *Aspergillus* species (such as *Aspergillus fumigatus, Aspergillus flavus* and *Aspergillus clavatus*), *Cryptococcus* sp. (such as *Cryptococcus neoformans, Cryptococcus gattii, Cryptococcus laurentii* and *Cryptococcus albidus*), a *Geotrichum* species, a *Saccharomyces* species, a *Hansenula* species, a *Candida* species (such as *Candida albicans*), a *Kluyveromyces* species, a *Debaryomyces* species, a *Pichia* species, or combination thereof. In certain example embodiments, the fungi is a mold. Example molds include, but are not limited to, a *Penicillium* species, a *Cladosporium* species, a *Byssochlamys* species, or a combination thereof.

Protozoa

In certain example embodiments, the pathogen is a protozoa. Examples of protozoa that can be detected in accordance with the disclosed methods and devices include without limitation any one or more of (or any combination of), Euglenozoa, Heterolobosea, Diplomonadida, Amoebozoa, *Blastocystis*, and Apicomplexa. Example Euglenozoa include, but are not limited to, *Trypanosoma cruzi* (Chagas disease), *T. brucei gambiense, T. brucei rhodesiense, Leishmania braziliensis, L. infantum, L. mexicana, L. major, L. tropica*, and *L. donovani*. Example Heterolobosea include, but are not limited to, *Naegleria fowleri*. Example Diplomonadida include, but are not limited to, *Giardia intestinalis* (*G. lamblia, G. duodenalis*). Example Amoebozoa include, but are not limited to, *Acanthamoeba castellanii, Balamuthia mandrillaris, Entamoeba histolytica*. Example Blastocysts include, but are not limited to, *Blastocystis hominis*. Example Apicomplexa include, but are not limited to, *Babesia microti, Cryptosporidium parvum, Cyclospora cayetanensis, Plasmodium falciparum, P. vivax, P. ovale, P. malariae*, and *Toxoplasma gondii.*

Parasites

In certain example embodiments, the pathogen is a parasite. Examples of parasites that can be detected in accordance with disclosed methods include without limitation one or more of (or any combination of), an *Onchocerca* species and a *Plasmodium* species.

Viruses

In certain example embodiments, the systems, devices, and methods, disclosed herein are directed to detecting viruses in a sample. The embodiments disclosed herein may be used to detect viral infection (e.g., of a subject or plant), or determination of a viral strain, including viral strains that differ by a single nucleotide polymorphism. The virus may be a DNA virus, an RNA virus, or a retrovirus. Non-limiting example of viruses useful with the present invention include, but are not limited to Ebola, measles, SARS, Chikungunya, hepatitis, Marburg, yellow fever, MERS, Dengue, Lassa, influenza, rhabdovirus or HIV. A hepatitis virus may include hepatitis A, hepatitis B, or hepatitis C. An influenza virus may include, for example, influenza A or influenza B. An HIV may include HIV 1 or HIV 2. In certain example embodiments, the viral sequence may be a human respiratory syncytial virus, Sudan ebola virus, Bundibugyo virus, Tai Forest ebola virus, Reston ebola virus, Achimota, Aedes flavivirus, Aguacate virus, Akabane virus, Alethinophid reptarenavirus, Allpahuayo mammarenavirus, Amapari mammarenavirus, Andes virus, Apoi virus, Aravan virus, Aroa virus, Arumwot virus, Atlantic salmon paramyxovirus, Australian bat lyssavirus, Avian bornavirus, Avian metapneumovirus, Avian paramyxoviruses, penguin or Falkland Islandsvirus, BK polyomavirus, Bagaza virus, Banna virus, Bat herpesvirus, Bat sapovirus, Bear Canon mammarenavirus, Beilong virus, Betacoronavirus, Betapapillomavirus 1-6, Bhanj a virus, Bokeloh bat lyssavirus, Borna disease virus, Bourbon virus, Bovine hepacivirus, Bovine parainfluenza virus 3, Bovine respiratory syncytial virus, Brazoran virus, Bunyamwera virus, Caliciviridae virus. California encephalitis virus, Candiru virus, Canine distemper virus, Canine pneumovirus, Cedar virus, Cell fusing agent virus, Cetacean morbillivirus, Chandipura virus, Chaoyang virus, Chapare mammarenavirus, Chikungunya virus, Colobus monkey papillomavirus, Colorado tick fever virus, Cowpox virus, Crimean-Congo hemorrhagic fever virus, Culex flavivirus, Cupixi mammarenavirus, Dengue virus, Dobrava-Belgrade virus, Donggang virus, Dugbe virus, Duvenhage virus, Eastern equine encephalitis virus, Entebbe bat virus, Enterovirus A-D, European bat lyssavirus 1-2, Eyach virus, Feline morbillivirus, Fer-de-Lance paramyxovirus, Fitzroy River virus, Flaviviridae virus, Flexal mammarenavirus, GB virus C, Gairo virus, Gemycircularvirus, Goose paramyxovirus SF02, Great Island virus, Guanarito mammarenavirus, Hantaan virus, Hantavirus Z10, Heartland virus, Hendra virus, Hepatitis A/B/C/E, Hepatitis delta virus, Human bocavirus, Human coronavirus, Human endogenous retrovirus K, Human enteric coronavirus, Human genital-associated circular DNA virus-1, Human herpesvirus 1-8, Human immunodeficiency virus 1/2, Human mastadenovirus A-G, Human papillomavirus, Human parainfluenza virus 1-4, Human parechovirus, Human picornavirus, Human smacovirus, Ikoma lyssavirus, Ilheus virus, Influenza A-C, Ippy mammarenavirus, Irkut virus, J-virus, JC polyomavirus, Japanese encephalitis virus, Junin mammarenavirus, KI polyomavirus, Kadipiro virus, Kamiti River virus, Kedougou virus, Khujand virus, Kokobera virus, Kyasanur forest disease virus, Lagos bat virus, Langat virus, Lassa mammarenavirus, Latino mammarenavirus, Leopards Hill virus, Liao ning virus, Ljungan virus, Lloviu virus, Louping ill virus, Lujo mammarenavirus, Luna mammarenavirus, Lunk virus, Lymphocytic choriomeningitis mammarenavirus, Lyssavirus Ozernoe, MS512\.225 virus, Machupo mammarenavirus, Mamastrovirus 1, Manzanilla virus, Mapuera virus, Marburg virus, Mayaro virus, Measles virus, Menangle virus, Mercadeo virus, Merkel cell polyomavirus, Middle East respiratory syndrome coronavirus, Mobala mammarenavirus, Modoc virus, Mojiang virus, Mokola virus, Monkeypox virus, Montana myotis leukoencephalitis virus, Mopeia lassa virus reassortant 29, Mopeia mammarenavirus, Morogoro virus, Mossman virus, Mumps virus, Murine pneumonia virus, Murray Valley encephalitis virus, Nariva virus, Newcastle disease virus, Nipah virus, Norwalk virus, Norway rat hepacivirus, Ntaya virus, O'nyong-nyong virus, Oliveros mammarenavirus, Omsk hemorrhagic fever virus, Oropouche virus, Parainfluenza virus 5, Parana mammarenavirus, Parramatta River virus, Peste-des-petits-ruminants virus, Pichande mammarenavirus, Picornaviridae virus, Pirital mammarenavirus, Piscihepevirus A, Porcine parainfluenza virus 1, porcine rubulavirus, Powassan virus, Primate T-lymphotropic virus 1-2, Primate erythroparvovirus 1, Punta Toro virus, Puumala virus, Quang Binh virus, Rabies virus, Razdan virus, Reptile bornavirus 1, Rhinovirus A-B, Rift Valley fever virus, Rinderpest virus, Rio Bravo virus, Rodent Torque Teno virus, Rodent hepacivirus, Ross River virus, Rotavirus A-I, Royal Farm virus, Rubella virus, Sabia mammarenavirus, Salem virus, Sandfly fever Naples virus, Sandfly fever Sicilian virus, Sapporo virus, Sathuperi virus, Seal anellovirus, Semliki Forest virus, Sendai virus, Seoul virus, Sepik virus, Severe acute respiratory syndrome-related coronavirus, Severe fever with thrombocytopenia syndrome virus, Shamonda virus, Shimoni bat virus, Shuni virus, Simbu virus, Simian torque teno virus, Simian virus 40-41, Sin Nombre virus, Sindbis virus, Small anellovirus, Sosuga virus, Spanish goat encephalitis virus, Spondweni virus, St. Louis encephalitis virus, Sunshine virus, TTV-like mini virus, Tacaribe mammarenavirus, Taila virus, Tamana bat virus, Tamiami mammarenavirus, Tembusu virus, Thogoto virus, Thottapalayam virus, Tick-borne encephalitis virus, Tioman virus, Togaviridae virus, Torque teno canis virus, Torque teno douroucouli virus, Torque teno felis virus, Torque teno midi virus, Torque teno sus virus, Torque teno tamarin virus, Torque teno virus, Torque teno 116 alophus virus, Tuhoko virus, Tula virus, Tupaia paramyxovirus, Usutu virus, Uukuniemi virus, Vaccinia virus, Variola virus, Venezuelan equine encephalitis virus, Vesicular stomatitis Indiana virus, WU Polyomavirus, Wesselsbron virus, West Caucasian bat virus, West Nile virus, Western equine encephalitis virus, Whitewater Arroyo mammarenavirus, Yellow fever virus, Yokose virus, Yug Bogdanovac virus, Zaire ebolavirus, Zika virus, or Zygosaccharomyces bailii virus Z viral sequence. Examples of RNA viruses that may be detected include one or more of (or any combination of) Coronaviridae virus, a Picornaviridae virus, a Caliciviridae virus, a Flaviviridae virus, a Togaviridae virus, a Bornaviridae, a Filoviridae, a Paramyxoviridae, a Pneumoviridae, a Rhabdoviridae, an Arenaviridae, a Bunyaviridae, an Orthomyxoviridae, or a Deltavirus. In certain example embodiments, the virus is Coronavirus, SARS, Poliovirus, Rhinovirus, Hepatitis A, Norwalk virus, Yellow fever virus, West Nile virus, Hepatitis C virus, Dengue fever virus, Zika virus, Rubella virus, Ross River virus, Sindbis virus, Chikungunya virus, Borna disease virus, Ebola virus, Marburg virus, Measles virus, Mumps virus, Nipah virus, Hendra virus, Newcastle disease virus, Human respiratory syncytial virus, Rabies virus, Lassa virus, Hantavirus, Crimean-Congo hemorrhagic fever virus, Influenza, or Hepatitis D virus.

In certain example embodiments, the virus may be a plant virus selected from the group comprising Tobacco mosaic virus (TMV), Tomato spotted wilt virus (TSWV), Cucumber mosaic virus (CMV), Potato virus Y (PVY), the RT virus Cauliflower mosaic virus (CaMV), Plum pox virus (PPV), Brome mosaic virus (BMV), Potato virus X (PVX), Citrus tristeza virus (CTV), Barley yellow dwarf virus (BYDV), Potato leafroll virus (PLRV), Tomato bushy stunt virus (TBSV), rice tungro spherical virus (RTSV), rice yellow mottle virus (RYMV), rice hoja blanca virus (RHBV), maize rayado fino virus (MRFV), maize dwarf mosaic virus (MDMV), sugarcane mosaic virus (SCMV), Sweet potato feathery mottle virus (SPFMV), sweet potato sunken vein closterovirus (SPSVV), Grapevine fanleaf virus (GFLV), Grapevine virus A (GVA), Grapevine virus B (GVB), Grapevine fleck virus (GFkV), Grapevine leafroll-associated virus-1, -2, and -3, (GLRaV-1, -2, and -3), Arabis mosaic virus (ArMV), or Rupestris stem pitting-associated virus (RSPaV). In a preferred embodiment, the target nucleic acid molecule is part of said pathogen or transcribed from a DNA molecule of said pathogen. For example, the target sequence may be comprised in the genome of an RNA virus.

In certain example embodiments, the virus may be a retrovirus. Example retroviruses that may be detected using the embodiments disclosed herein include one or more of or any combination of viruses of the Genus Alpharetrovirus, Betaretrovirus, Gammaretrovirus, Deltaretrovirus, Epsilonretrovirus, Lentivirus, Spumavirus, or the Family Metaviridae, Pseudoviridae, and Retroviridae (including HIV), Hepadnaviridae (including Hepatitis B virus), and Caulimoviridae (including Cauliflower mosaic virus)

In certain example embodiments, the virus is a DNA virus. Example DNA viruses that may be detected using the embodiments disclosed herein include one or more of (or any combination of) viruses from the Family Myoviridae, Podoviridae, Siphoviridae, Alloherpesviridae, Herpesviridae (including human herpes virus, and Varicella Zoster virus), Malocoherpesviridae, Lipothrixviridae, Rudiviridae, Adenoviridae, Ampullaviridae, Ascoviridae, Asfarviridae (including African swine fever virus), Baculoviridae, Cicaudaviridae, Clavaviridae, Corticoviridae, Fuselloviridae, Globuloviridae, Guttaviridae, Hytrosaviridae, Iridoviridae, Marseilleviridae, Mimiviridae, Nudiviridae, Nimaviridae, Pandoraviridae, Papillomaviridae, Phycodnaviridae, Plasmaviridae, Polydnaviruses, Polyomaviridae (including Simian virus 40, JC virus, BK virus), Poxviridae (including Cowpox and smallpox), Sphaerolipoviridae, Tectiviridae, Turriviridae, Dinodnavirus, Salterprovirus, Rhizidiovirus, among others *Escherichia coli, Klebsiella pneumoniae, Pseudomonas aeruginosa, Staphylococcus aureus, Acinetobacter baumannii, Candida albicans, Enterobacter cloacae, Enterococcus faecalis, Enterococcus faecium, Proteus mirabilis, Staphylococcus agalactiae*, or *Staphylococcus maltophilia* or a combination thereof.

Malaria Detection and Monitoring

Malaria is a mosquito-borne pathology caused by *Plasmodium* parasites. The parasites are spread to people through the bites of infected female Anopheles mosquitoes. Five *Plasmodium* species cause malaria in humans: *Plasmodium falciparum, Plasmodium vivax, Plasmodium ovale, Plasmodium malariae*, and *Plasmodium knowlesi.*

The invention is further illustrated by the following non-limiting examples.

The following Materials and Methods were used in the Examples that follow.

Reagents and Samples

Cas12a (100 μM), deoxynucleotide (dNTP) mix (10 mM of each), AMV reverse transcriptase (10,000 U/mL) and nuclease-free water were purchased from New England BioLabs® (Ipswich, MA). The crRNAs for the N and S genes of SARS-CoV-2 as well as the Human RNAse P gene were synthesized from Integrated DNA Technologies® (IDT) (Coralville, IA). TEMED, $(NH_4)_2S_2O_8$, 30% acrylamide/bis-acrylamide solution, and 10×TBE Buffer were purchased from Bio-Rad Laboratories (Hercules, CA). Clear resin (FLGPCL02) was purchased from Formlabs. The quantitative PCR (qPCR) control RNA from heat inactivated SARS-CoV-2 (NR-52347) was obtained from the BEI Resources. TwistAmp® Basic Kit was purchased from TwistDx™ Limited (Maidenhead, UK). The clinical swab samples were de-identified and in compliance with ethical regulations and the approval of Institutional Review Board of the University of Health Center (protocol #: P61067). All chemicals used were analytical reagent grade or better.

SARS-CoV-2 Detection by RT-RPA/CRISPR-Cas12a Assay

RT-RPA/CRISPR-Cas12a detection of the N and S gene of SARS-CoV-2 in reaction tubes was carried out as described in a previous study. First, multiple RPA amplification reaction was carried out at 37° C. for 15 min with 0.48 μM RPA forward and reverse primer of the N gene of SARS-CoV-2, 0.48 μM RPA forward and reverse primer of the S gene of SARS-CoV-2, 14 mM magnesium acetate, 2 U of AMV reverse transcriptase, 1 μL SARS-CoV-2 RNA target and TwistAmp® Basic reagent. Next, 2 μL RPA amplicons was distributed into individual reaction tube containing 13 μL CRISPR-Cas12a detection solution (100 nM Cas12a, 62.5 nM specific crRNA, 50 nM ssDNA-FQ reporter in reaction buffer) for CRISPR-based fluorescence detection. At the end of 25-min incubation reaction at 37° C., the endpoint images were taken by either ChemiDoc™ MP Imaging System or LED blue light illuminator (Maestrogen UltraSlim®). The fluorescence intensity data was analyzed by Image J.

Fabrication of Autonomous Lab-On-Paper System

The RPA amplification reactor was designed by using SolidWorks software and fabricated on a Form 2 3D printer (Formlabs) with clear methacrylate-based resin (Formlabs, FLGPCL02). The paper-based CRISPR detection chambers and paper-based sucrose valve were designed by using SolidWorks software and printed on the Whatman® Grade 1 paper using black wax by Xerox™ Colorqube™ 8870 printer. After printing, the paper-based CRISPR detection chambers were put on one hot plate for 30 seconds at 120° C., allowing the printed wax to melt and penetrate through the paper-based cellulose membrane. For paper-based CRISPR detection chambers, each chamber was added with 2 μL CRISPR reaction solution. For the fabrication of the sucrose valve, sucrose solution at different concentrations (5-15%) was added on the paper-based valve and dried at room temperature for 24 h. Then, the sucrose solution was added again on another side. Lastly, the 3D printed RPA amplification reactor, paper-based sucrose valve and paper-based CRISPR detection chambers were assembled by the 3M double-sided tape (9500 PC) and PCR Sealers tape (Microseal® 'B' Film) (Bio-Rad).

Lyophilization of CRISPR-Cas12a Reagents on Paper-Based CRISPR Chambers

The CRISPR-Cas12a reaction reagents contain 1 μM Cas12a, 500 nM ssDNA-FQ reporter, 10% trehalose solution. In our lab-on-paper system, 1 μL CRISPR-Cas12a reaction solution was pre-loaded on each reaction chamber of the paper-based microfluidics and lyophilized at −80° C. for 1 h using freeze-drying system (FreeZone 2.5 liter benchtop, Labconco®). For SARS-CoV-2 detection, 0.625 μM crRNAs for SARS-CoV-2 N gene and S gene were, respectively added into CRISPR-Cas12a reaction solution.

For housekeeping gene detection, 0.625 μM crRNA of human RNAse P gene was introduced into CRISPR-Cas12a reaction solution and lyophilized on the RNAse P gene detection chamber. For blank control, no crRNA was added into CRISPR-Cas12a reaction reagents.

Operation and Sensitivity Analysis of Autonomous Lab-On-Paper System

To investigate the sensitivity of SARS-CoV-2 detection on the lab-on-paper system, ten-fold serial dilutions of SARS-CoV-2 RNA from 0 to $10^4$ copies per test were first mixed with 25 μL RPA reaction solutions containing specific forward and reverse primers. After the mixture was added into the RPA amplification reactor, the reactor was sealed by the PCR Sealers tape (Microseal® 'B' Film) to avoid the aerosol contamination. Next, the autonomous lab-on-paper system was incubated on the heating plate at 37° C. for 40 min. After the incubation reaction, the endpoint images of the lab-on-paper system were taken by ChemiDoc™ MP Imaging System. The fluorescence intensity data of the CRISPR detection chambers was analyzed by Image J. The highest fluorescence intensity of positive signal collected was applied as the standard for the normalized fluorescence calculation. The test result was defined as positive if the normalized fluorescence was three standard deviation above the mean normalized fluorescence of the negative groups.

Multiple Gene Detection of SARS-CoV-2 in Clinical Swab Samples

To investigate the clinical utility of the autonomous lab-on-paper system for multiplex-gene detection, 21 de-identified clinical swab samples (including eight COVID-19 positive samples) were detected. Their viral RNAs were extracted by QIAamp® DSP Viral RNA Mini Kit (QIAGEN N.V., Venlo) according to its instruction. 1 μL of RNA extracts was used for multiple detection in the autonomous lab-on-paper system. After incubation at 37° C. for 40 min, the images of the lab-on-chip system were taken by the ChemiDoc™ MP Imaging System.

Figure 1B:
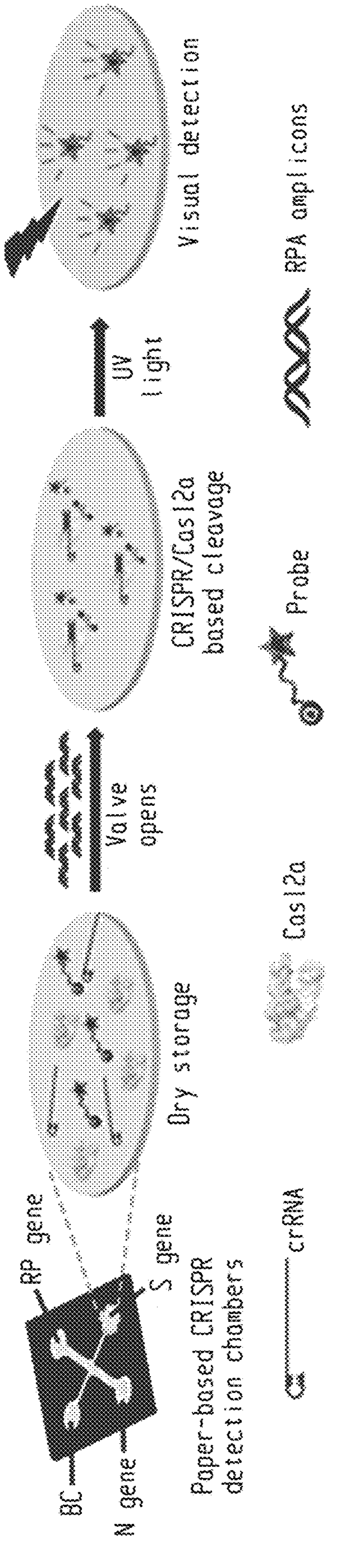
Figure 1C:
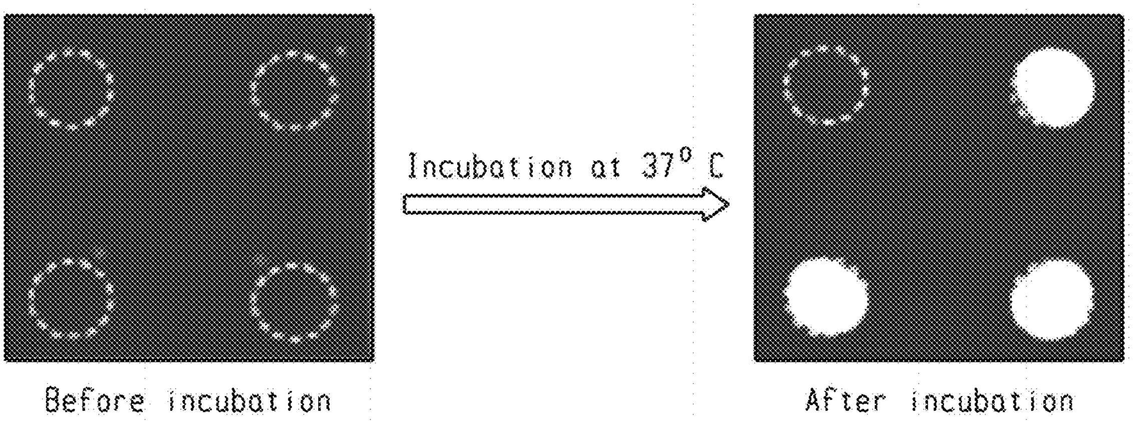
Figure 1D:
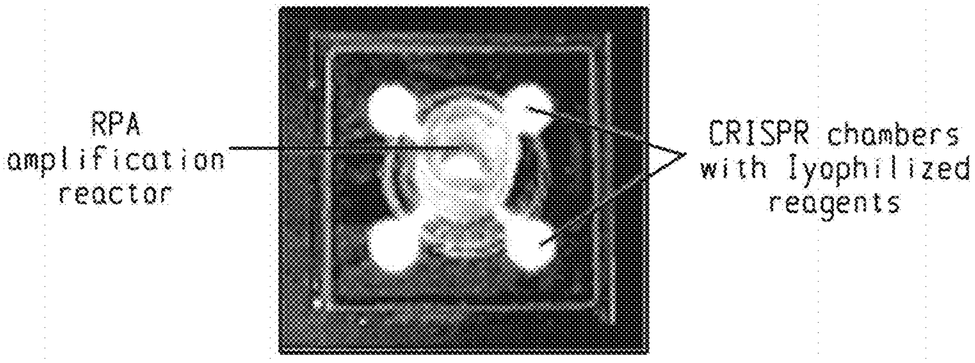

Example 1: Lab-On-Paper System for Multiplex Detection of Target Pathogen Nucleic Acids The novel CRISPR-Cas detection system combing target nucleic acid pre-amplification and CRISPR-Cas-based signal generation has emerged as a next-generation of nucleic acid-based molecular diagnosis technique. However, these detection methods typically require separate and multiple manual operations, such as amplification products transferring, which not only complicates the testing procedures but increases the risk of carry-over contaminations. To overcome these challenges, an autonomous lab-on-paper has been established for simple, rapid, automated, and multiplex gene diagnosis of SARS-CoV-2. As shown in FIG. 1A, the autonomous lab-on-paper system mainly consists of: i) 3D printed RPA amplification reactor for multiple RPA amplification, ii) paper-based sucrose valve, and iii) paper-based CRISPR-Cas12a detection chambers. The 3D printed RPA amplification reactor and paper-based CRISPR detection chambers are physically separated by the sucrose valve, which is normally closed and automatically opens after RPA amplification at a pre-set time (e.g., 15 min) due to dissolving of sucrose in the paper-based valve. As shown in FIG. 1B, the CRISPR-Cas12a reaction solution was pre-loaded and lyophilized on the paper-based CRISPR detection chambers. After the valve opens, RPA amplicons automatically migrates to the CRISPR detection chambers. The migrated amplicons specifically trigger the non-specific cleavage activity of CRISPR-Cas12a, which further cleaves the fluorophore quencher (FQ)-labeled ssDNA probe and generates strong fluorescent signals for detection. As shown in FIG. 1C, the fluorescent signal can be directly read by the naked eye or recorded by smartphone camera. As a low-cost diagnostics technology, the developed lab-on-chip system provides a simple, sensitive and accurate approach for comprehensive COVID-19 screening, especially in resource-limited settings.

Example 2: SARS-CoV-2 Detection by RT-RPA/CRISPR-CAS12a Assay

Figure 2A:
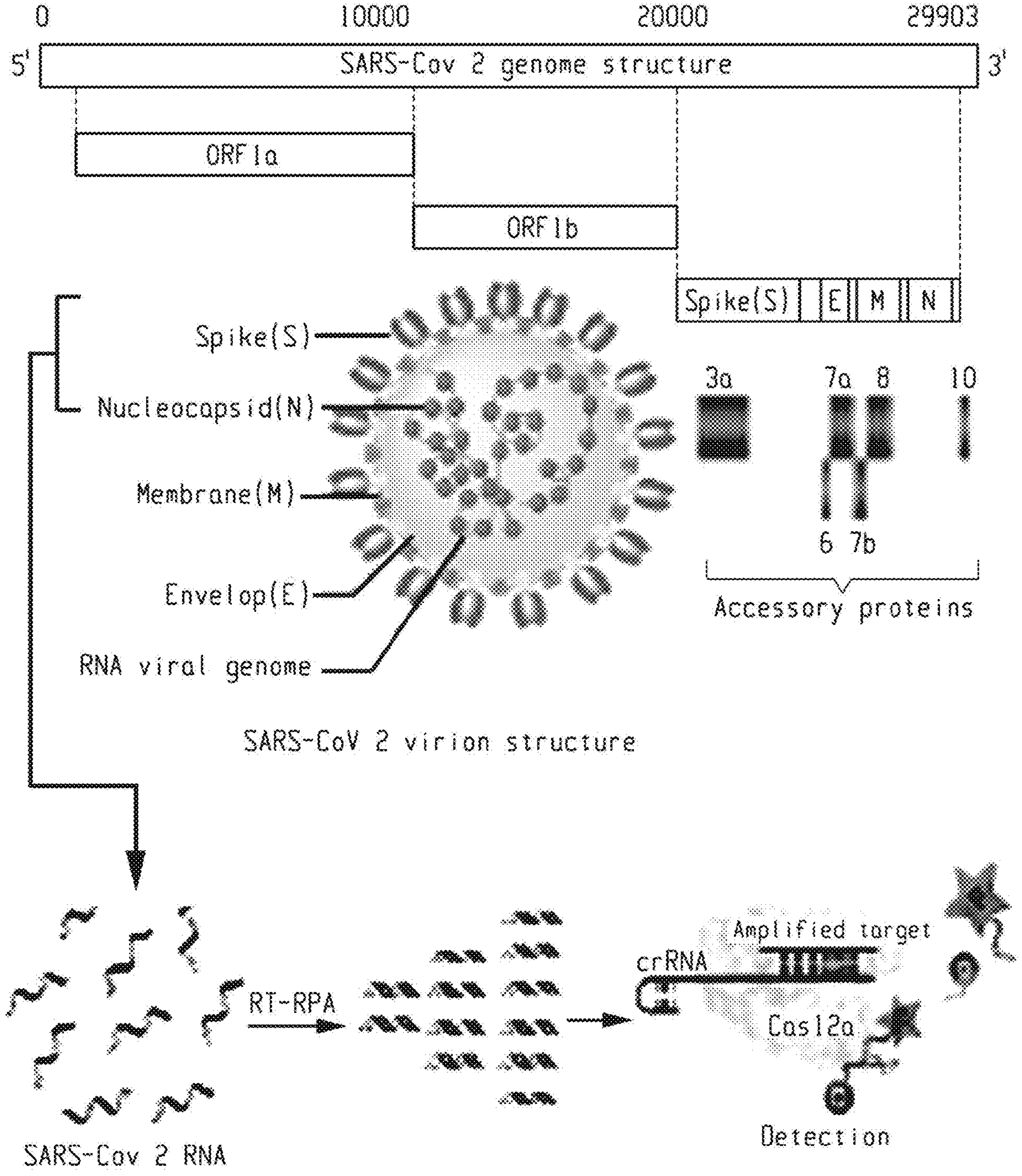
FIG. 2A-D illustrate detection of SARS-CoV-2 by RT-RPA/CRISPR-Cas12a assay in reaction tubes. 2A is a schematic showing the target genes and detection strategy of SARS-CoV. 2B shows fluorescence detection of N and S genes of SARS-CoV-2 by RT-RPA/CRISPR-Cas12a assay. NC, negative control without SARS-Cov-2 RNA. Tubes 1-4 contain, respectively, 1, 10, $10^2$, $10^3$ copies SARS-CoV-2 RNA spiked in the reaction solution. The images were taken under the LED blue transilluminator and ChemiDoc™ MP Imaging System, respectively. 2C shows threshold time of the N gene detection of SARS-CoV-2 at different concentrations (0, 1, 10, $10^2$, $10^3$ copies). 2D shows threshold time of the S gene detection of SARS-CoV-2 at different concentrations (0, 1, 10, $10^2$, $10^3$ copies). *** indicate a significant difference of the NC and 1 copy with 10 to $10^3$ copies SARS-CoV-2 in the reaction solution ($p<0.001$, t-test). Error bars denote s.d. (n=3).
Figure 2B:
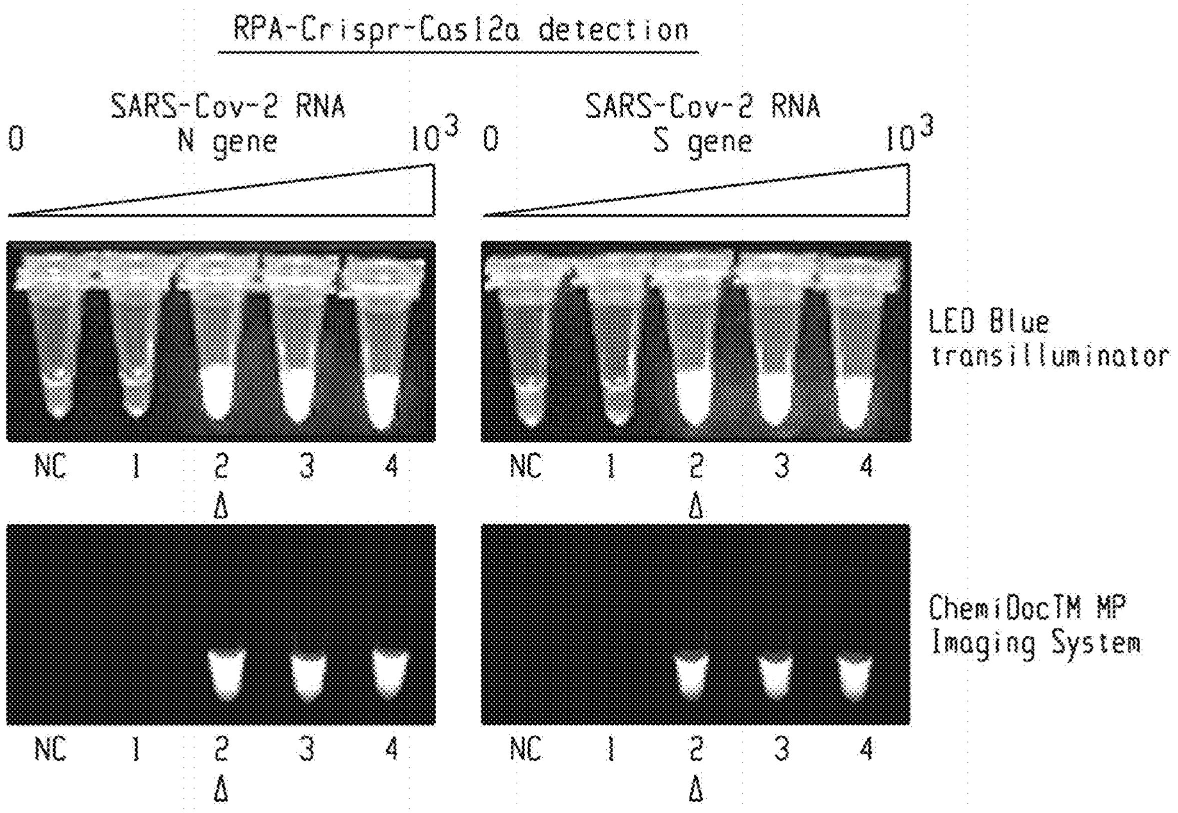
Figure 2C:
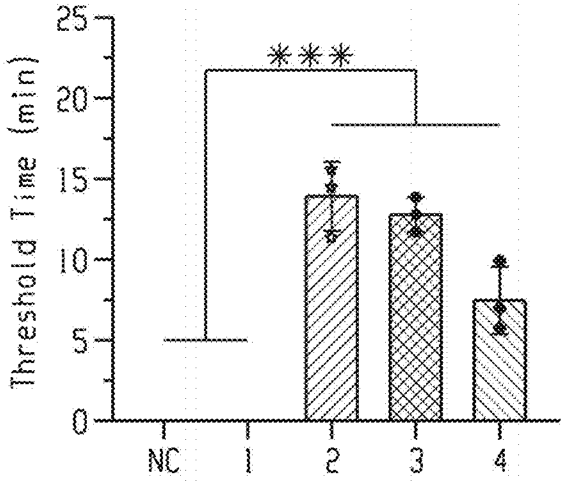
Figure 2D:
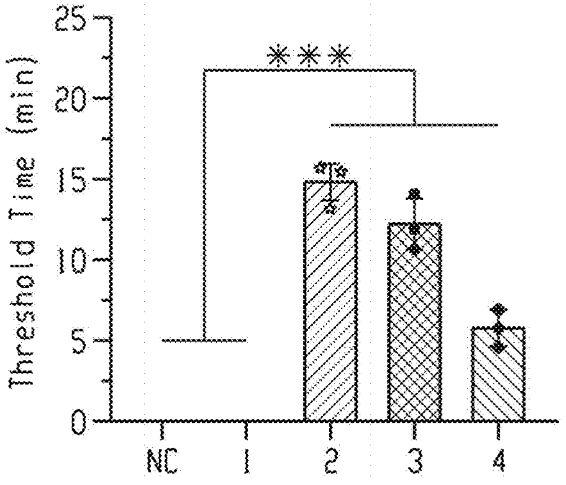

The COVID-19 pandemic caused by the SARS-CoV-2, has seriously threatened human health. The early screening based on molecular diagnosis technology is an effective approach to prevent the rapid spread of SARS-CoV-2 virus. Here, RT-RPA/CRISPR-Cas12a system was applied for rapid, sensitive detection of SARS-CoV-2 by targeting its N and S genes (FIG. 2A). Before adapting the RT-RPA/CRISPR-Cas12a assay to our lab-on-paper system, we first investigated the detection performance of the RT-RPA/CRISPR-Cas12a assay for SARS-CoV-2 detection in the reaction tubes. The Cas12 guide RNAs (gRNAs) to the SARS-CoV-2 were designed following the previous studies (Table 1). Because CRISPR-based fluorescence detection itself lacks multiple detection ability, the RPA amplicons were separately added into individual reaction tubes for CRISPR-based fluorescence detection after 15-min RPA amplification incubation. As shown in FIG. 2B, we could detect N gene and S gene of 10 copies SARS-CoV-2 RNA per test (n=3). In addition, the fluorescent signal can be collected by the fluorescence imaging system and be directly recognized by the naked eye under the LED blue light illuminator.

Example 3: Optimization of Autonomous Lab-On-Paper System

Figure 3A:
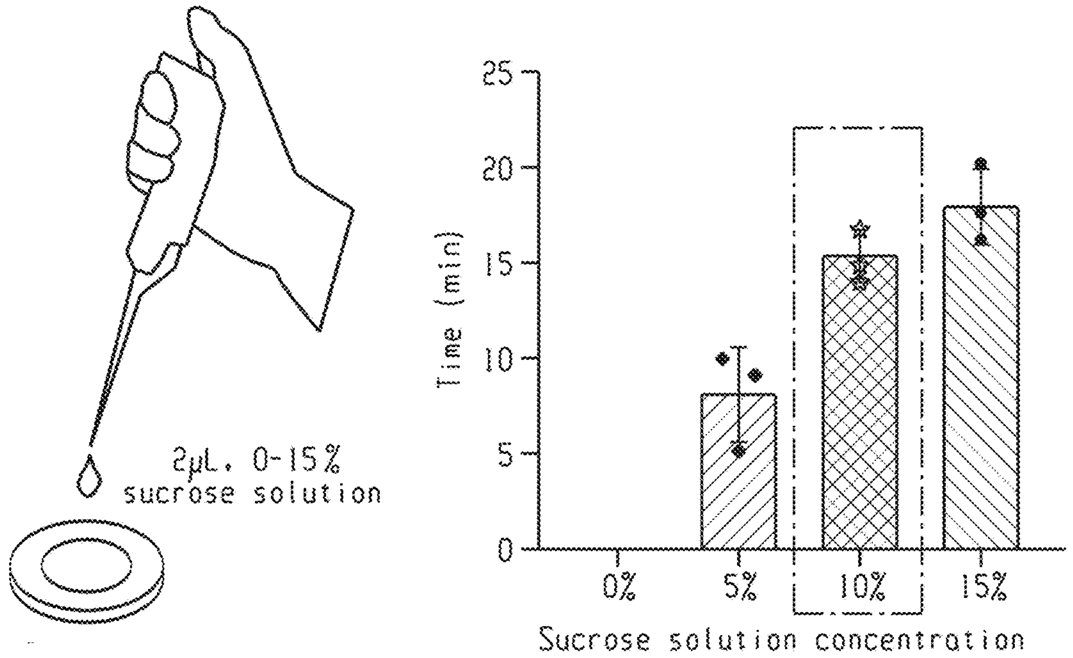
FIG. 3A-B illustrate the method of optimization of the concentration of sucrose solution used for the paper-based sucrose valve. 3A is a schematic showing $ddH_2O$ (0%), 5%, 10% and 15% sucrose solution were dropped and dried on the both sides of the paper-based valve, respectively. 3B shows fluorescence detection of SARS-CoV-2 on the autonomous lab-on-paper system at different incubation times. *** indicate a significant difference ($p<0.001$, t-test). Error bars denote s.d. (n=3).
Figure 6:
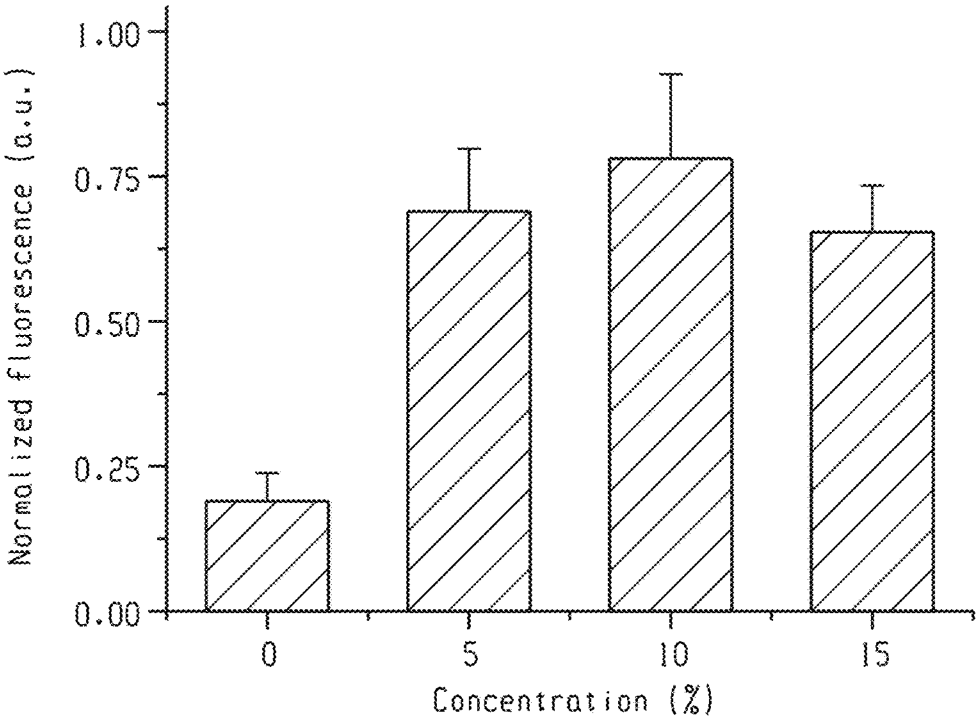
FIG. 6 shows optimization of the trehalose's concentration for dry storage of CRISPR reagents. Error bars denote s.d. (n=3).
Figure 7:
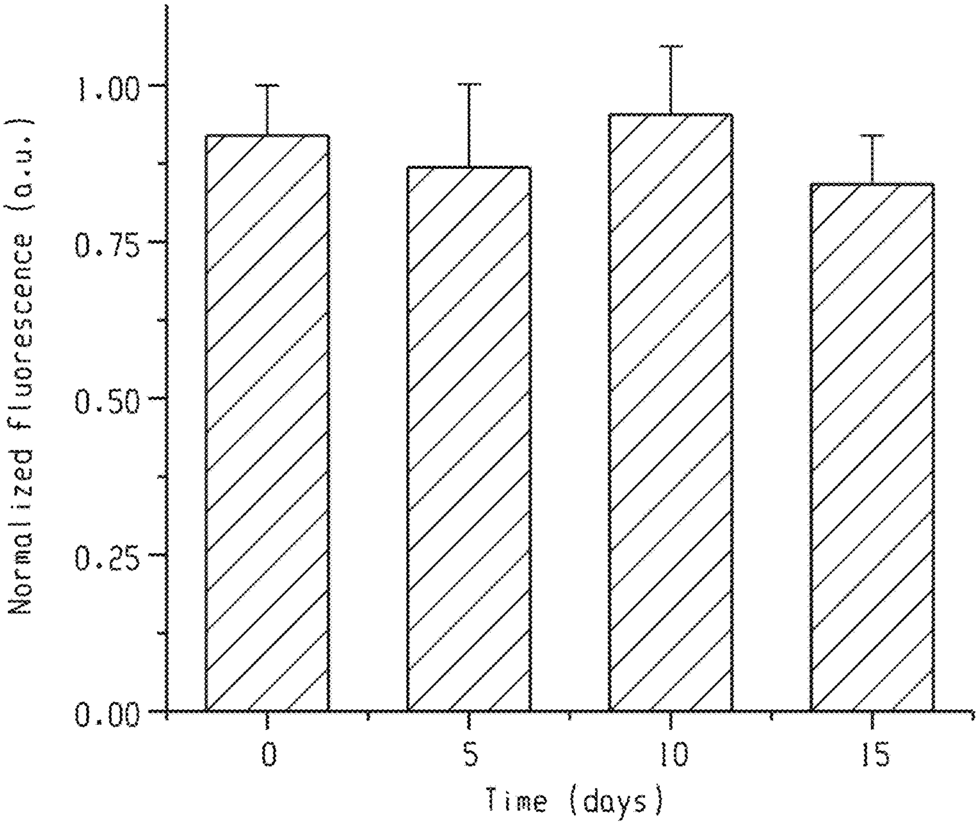
FIG. 7 shows stability of pre-stored CRISPR/Cas12a reagents on the paper-based detection chambers. Error bars denote s.d. (n=3).

To achieve simple and integrated detection of SARS-CoV-2, an autonomous lab-on-paper system was established for multiple gene diagnosis. In our lab-on-paper system, multiple RPA amplification reaction was firstly carried out in the RPA amplification reactor when the sucrose valve was initially closed. When the sucrose on the paper-based valve was totally dissolved, the paper-based sucrose valve opened, which brought the RPA amplification reactor and CRISPR detection chambers connected with each other. To optimize the opening time of the paper-based sucrose valve, different sucrose concentrations ranging from 5 to 15% were investigated in our lab-on-paper system. As shown in FIG. 3A, the higher the sucrose concentration, the longer the valve's opening time. Also, the sucrose valves exhibited satisfactory reliability. In our assay, 15-minute RPA incubation provides enough RPA amplicons for downstream CRISPR-based fluorescence detection. Thus, 10% sucrose solution was used to fabricate the paper-based sucrose valve of our lab-on-paper system. To improve the lyophilized Cas12a's activity, trehalose was added into the CRISPR reaction solution before lyophilization on the paper-based CRISPR detection chambers. As shown in FIG. 6, 10% trehalose solution showed the best performance in our lab-on-paper system. To demonstrate the feasibility of our lab-on-paper system for diagnostics without need for a cold chain, we evaluated and tested the lyophilized CRISPR reagents on the CRISPR detection chamber at room temperature for at least 30 days. As shown in FIG. 7, there was no significant decrease of fluorescence signals over a 30-day period at room temperature. Therefore, the experimental results show that our lab-on-paper system can be transported at room temperature and has a potential for diagnostic applications in resource-limited settings.

Figure 3B:
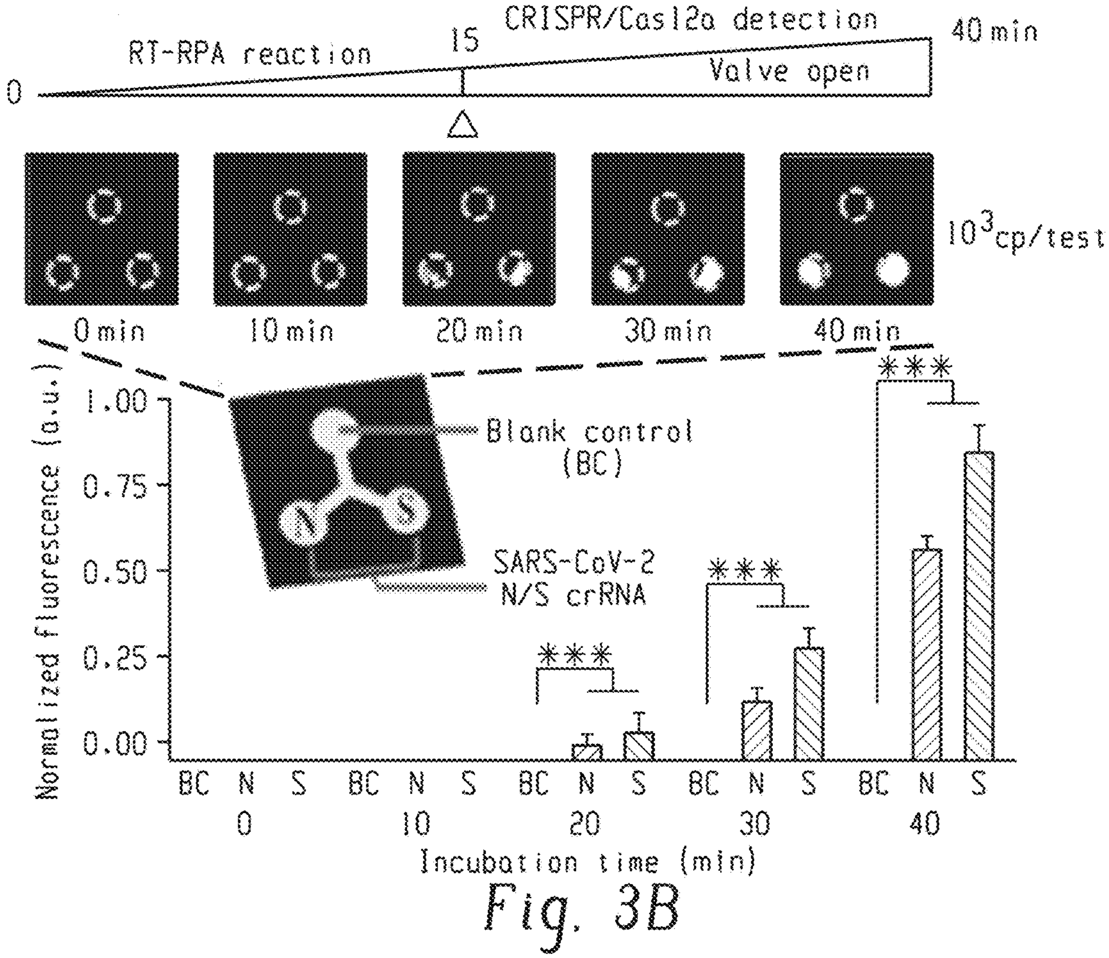
Figure 4A:
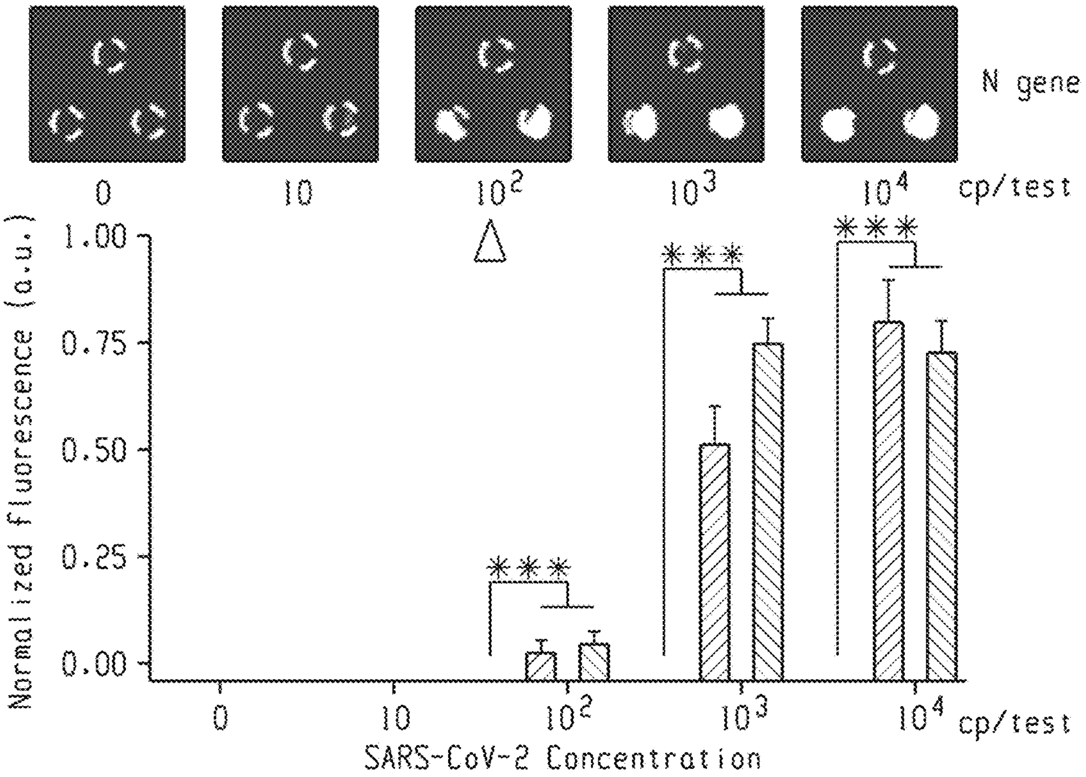
FIG. 4A-B show results of SARS-CoV-2 detection on the autonomous lab-on-paper system. 4A shows detection sensitivity for N genes of SARS-CoV-2 on the lab-on-paper system. 4B shows detection sensitivity for S genes of SARS-CoV-2 on the lab-on-paper system. *** indicates a significant difference in the fluorescent intensity ($p<0.001$, t-test). Error bars denote s.d. (n=5).
Figure 4B:
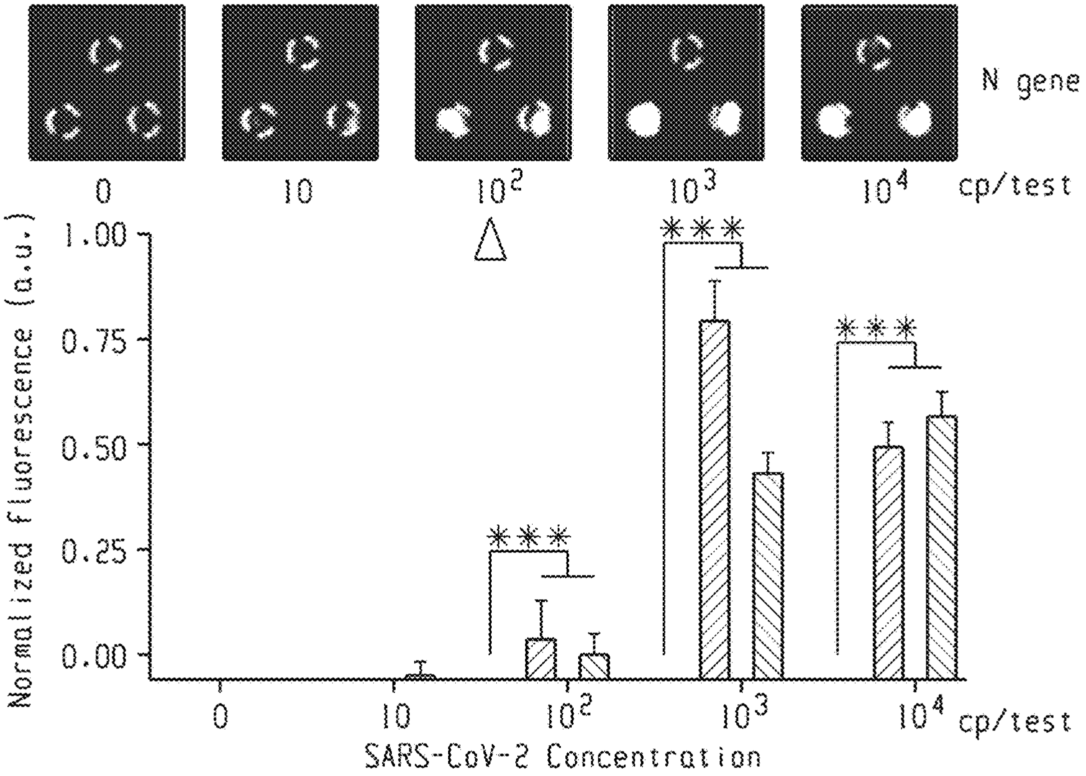

To optimize the detection time of the autonomous lab-on-paper system, $10^3$ copies SARS-CoV-2 RNA per test was added into the RPA amplification reactor and incubated at 370° C. for different time (e.g., 10, 20, 30 and 40 min). As shown in FIG. 3B, no fluorescence signal was observed within 15 min-incubation, which should be attributed to the initial closing of the sucrose valve. With the increasing of the incubation time, the fluorescence signals of the CRISPR detection chambers become stronger and stronger. After 40 min incubation, the strong fluorescent signals can be obviously observed on the positive CRISPR chambers, which indicates that 40 min-incubation is enough for our lab-on-paper system. To further investigate the sensitivity of the developed lab-on-paper system for SARS-CoV-2 detection, tenfold serial dilutions of SARS-CoV-2 RNA from 0 to $10^4$ copies per test were added into the RPA amplification reactor of the lab-on-paper system. As shown in FIG. 4, $10^2$ copies SARS-CoV-2 RNA per test could be detected by targeting both N and S genes on the lab-on-paper system. Additionally, we observed 0 occurrences of nonspecific amplification out of 5 no-template controls for both N and S genes detection, obtaining a specificity of 100%. Further, the fluorescent intensity of the CRISPR detection chambers was analyzed by the Image J. As shown in FIG. 4, the SARS-CoV-2 RNA concentration from $10^2$ to $10^4$ copies per test showed a significant difference with blank control groups.

Example 4: Multiple Gene Detection of SARS-COV-2 from Clinical Swab Samples

Figure 5A:
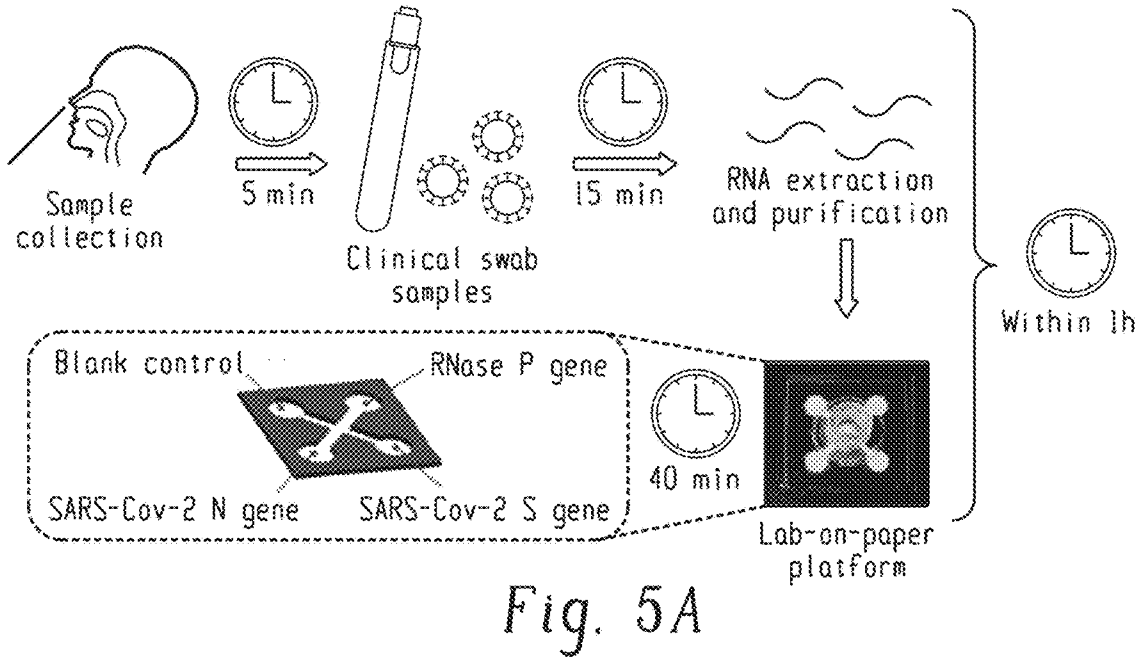
FIG. 5A-B illustrate multiple gene diagnosis of SARS-CoV-2 from clinical human swab samples using the system and methods described herein. 5A is a schematic of workflow and testing time for SARS-CoV-2 detection in clinical swab samples by using the autonomous lab-on-paper system. 5B shows multiple gene diagnosis results of SARS-CoV-2 from 21 clinical swab samples on the autonomous lab-on-paper system. BC, blank control. RP gene, RNase P gene.
Figure 5B:
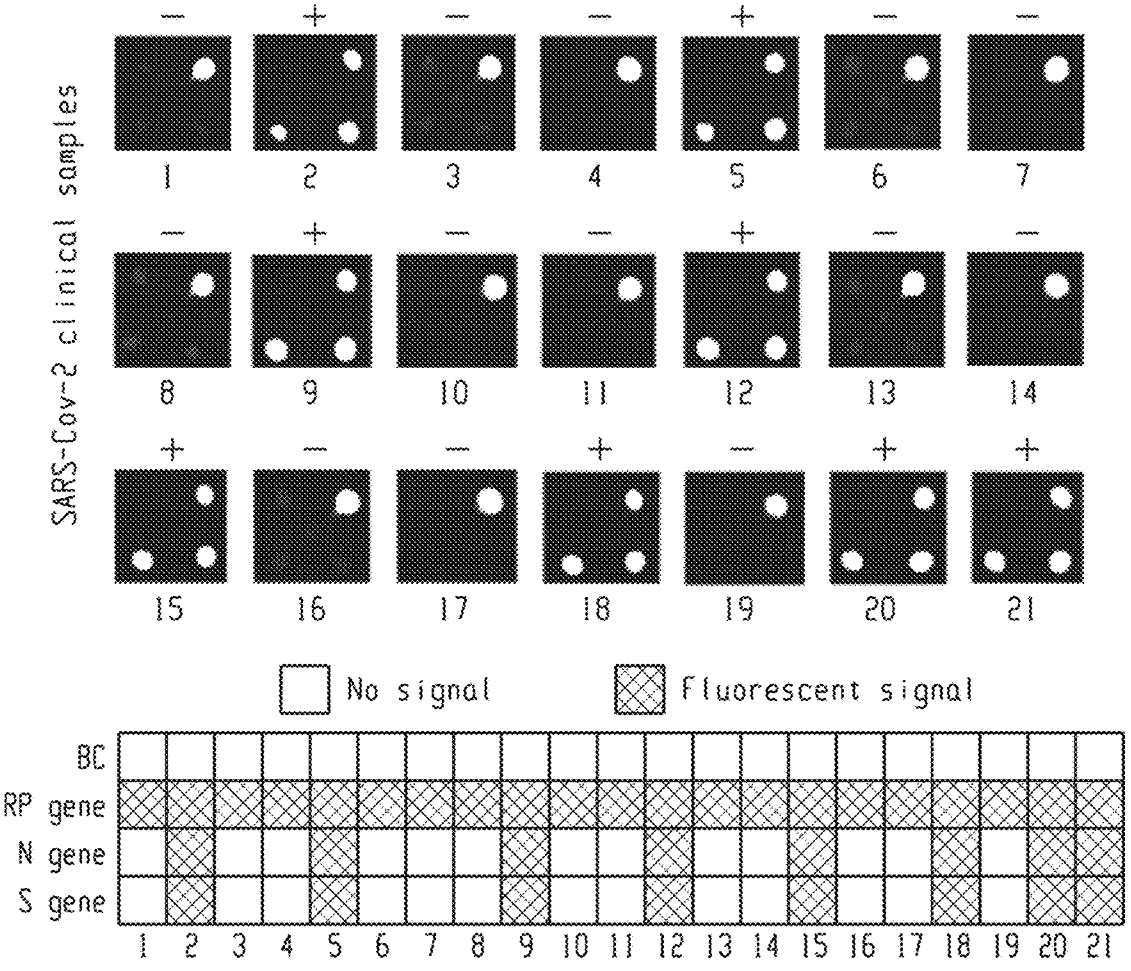

To evaluate the clinical feasibility of the developed autonomous lab-on-paper system for multiple gene detection of SARS-CoV-2, the RNA samples extracted from 21 nasopharyngeal swab clinical samples were tested. Among them, there were 8 SARS-CoV-2 positive samples and 13 SARS-CoV-2 negative samples which have been confirmed by RT-PCR method (Table 2). The detection workflow of the lab-on-paper system for clinical swab samples is shown in FIG. 5A. Total turnaround time including nucleic acid preparation is less than 1 hour. To achieve an accurate nucleic acid-based molecular detection, it is crucial to simultaneously detect the housekeeping gene as an internal control to verify and monitor the test performance. The internal control can validate whole diagnostic workflows, including nucleic acid sample preparation, multiplex RT-RPA reaction, lyophilized reagent quality and CRISPR-based fluorescence detection. We detected RNA extracts of 21 nasopharyngeal swab samples using our lab-on-paper system. As shown in FIG. 5B, for all 8 positive samples, both N and S genes of SARS-CoV-2, and housekeeping RNAse P gene were simultaneously detected on the lab-on-paper system, which is comparable with that of RT-PCR method. On the contrary, for 13 negative samples, only human RNase P gene was detected. We did not observe nonspecific signals of 13 negative clinical samples, which may be attributed to high specificity of CRISPR detection. The detection of the housekeeping RNAse P gene in clinical samples indicates that high quality nucleic acid samples were extracted from the clinical samples. Therefore, these results indicated that the established lab-on-paper system could simultaneously detect multiple genes for SARS-CoV-2 diagnostics in a single clinical sample, which further improved detection accuracy and reliability. To our best knowledge, it is the first time to achieve CRISPR-based multi-gene detection of SARS-CoV-2 on paper-based microfluidics system.

TABLE 2

CT VALUES OF REAL-TIME RT-PCR FOR N GENE DETECTION OF SARS-COV-2 IN CLINICAL SAMPLES.

| Samples | Ct values |
|---|---|
| 1 | Not Detected |
| 2 | 29 |
| 3 | Not Detected |
| 4 | Not Detected |
| 5 | 23 |
| 6 | Not Detected |
| 7 | Not Detected |
| 8 | Not Detected |
| 9 | 21 |
| 10 | Not Detected |
| 11 | Not Detected |
| 12 | 19 |
| 13 | Not Detected |
| 14 | Not Detected |
| 15 | 16 |
| 16 | Not Detected |
| 17 | Not Detected |
| 18 | 20 |
| 19 | Not Detected |
| 20 | 18 |
| 21 | 27 |

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. "About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±10% or 5% of the stated value. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed No language in the specification should be construed as indicating any non-claimed element as essential to the practice of the invention as used herein.

"One or more," as used herein, means at least one, and thus includes individual components as well as mixtures/combinations.

Other than in the operating examples, or where otherwise indicated, all numbers expressing quantities of ingredients and/or reaction conditions are to be understood as being modified in all instances by the term “about,” meaning within 10% of the indicated number (e.g., “about 10%” means 9%-11% and “about 2%” means 1.8%-2.2%).

All percentages and ratios are calculated by weight unless otherwise indicated. All percentages are calculated based on the total composition unless otherwise indicated. Generally, unless otherwise expressly stated herein, “weight” or “amount” as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

All ranges and amounts given herein are intended to include subranges and amounts using any disclosed point as an end point. Thus, a range of “1% to 10%, such as 2% to 8%, such as 3% to 5%,” is intended to encompass ranges of “1% to 8%,” “1% to 5%,” “2% to 10%,” and so on. All numbers, amounts, ranges, etc., are intended to be modified by the term “about,” whether or not so expressly stated. Similarly, a range given of “about 1% to 10%” is intended to have the term “about” modifying both the 1% and the 10% endpoints. Further, it is understood that when an amount of a component is given, it is intended to signify the amount of the active material unless otherwise specifically stated.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A pathogen nucleic acid detection system, comprising, in fluid communication, a recombinase polymerase amplification (RPA) reaction chamber for producing RPA amplification products, comprising reagents for multiplex amplification of one or more target pathogen nucleic acids, a microfluidic chip comprising multiplexed detection chambers, wherein each detection chamber comprises a cleavable nucleic acid probe and detection reagents, the detection reagents comprising (i) a clustered regularly interspaced short palindromic repeat-associated nuclease 12a (CRISPR/Cas12a) enzyme, and (ii) a guide ribonucleic acid RNA (gRNA) specific for one target pathogen nucleic acid of the one or more target pathogen nucleic acids, and a dissolvable valve configured for controlling flow of the RPA amplification products from the RPA reaction chamber to the microfluidic chip, wherein, when not dissolved, the dissolvable valve is configured to stop the passage of the RPA amplification products to the microfluidic chip, and when dissolved, the dissolvable valve is configured to provide passage of the RPA amplification products to the microfluidic chip to initiate CRISPR/Cas1 12a nonspecific cleavage of the cleavable nucleic acid probe, wherein a detectable signal is generated in the detection chambers when the cleavable nucleic acid probe is cleaved by the CRISPR/Cas12a and wherein the detectable signal indicated the presence of the one or more target pathogen nucleic acids, and wherein the dissolvable valve comprises a valve material and a dissolvable material, and the dissolvable material comprises sucrose, trehalose, polyvinylpyrrolidone (PVP), polyethylene glycol (PEG), or mixtures thereof.

2. The detection system of claim 1, wherein the cleavable nucleic acid probe is a fluorophore-quencher-labeled ssDNA probe.

3. The detection system of claim 1, wherein the multiplexed detection chamber is a multiplexed paper detection chamber.

4. The detection system of claim 3, wherein the reagents in the multiplexed detection chamber are lyophilized.

5. The detection system of claim 1, wherein the pathogen nucleic acid is from a severe acute respiratory syndrome coronavirus 2 (SARS-COV-2).

6. The detection system of claim 5, wherein the SARS-CoV-2 nucleic acid is a nucleocapsid (N) gene or a spike(S) gene.

7. The detection system of claim 6, wherein the detection reagents include a SARS-COV-2 N gene single guide RNA (sgRNA) having SEQ ID NO: 3, and a SARS-COV-2 spike(S) gene sgRNA having SEQ ID NO:6.

8. The detection system of claim 1, wherein the dissolvable valve is a sucrose-based dissolvable valve.

9. The detection system of claim 1, wherein the system further comprises a sample-collecting component that is a self-administered sample-collecting component.

10. The detection system of claim 1, wherein each component of the detection system is stable at room temperature or does not require cold chain storage.

11. The detection system of claim 1, wherein a detectable signal is generated after 40 minutes of incubation.

12. The detection system of claim 1, wherein the detection reagents include trehalose.

13. The detection system of claim 1, wherein the detection system can detect $10^2$ copies of the target pathogen nucleic acid.

14. The detection system of claim 1, wherein the multiplex amplification is an isothermal amplification.

15. The system of claim 14, wherein the reagents for RPA multiplex amplification comprise a reverse transcriptase, a forward and reverse primer for severe acute respiratory syndrome coronavirus 2 (SARS-COV-2) nucleocapsid (N) gene having SEQ ID NO:1 and SEQ ID NO:2, respectively, and a forward and reverse primer for SARS-COV-2 spike(S) gene having SEQ ID NO: 4 and SEQ ID NO: 5, respectively.

16. A method for detecting a pathogen in a sample or a set of samples collected from a subject or subjects with the pathogen nucleic acid detection system of claim 1, comprising depositing the sample or set of samples in the RPA reaction chamber of the pathogen nucleic acid detection system, amplifying the one or more target pathogen nucleic acids in each sample to produce RPA amplification products for each sample, the dissolvable valve dissolving and passing the RPA amplification products through the valve to the microfluidic chip thus initiating CRISPR/Cas 12a nonspecific cleavage of the cleavable nucleic acid probe, and detecting the detectable signal generated in the multiplexed detection chamber, wherein the detectable signal indicates presence of the target pathogen nucleic acid and presence of the pathogen in the sample, and wherein the dissolvable valve comprises a valve material and a dissolvable material, and the dissolvable material comprises sucrose, trehalose, polyvinylpyrrolidone (PVP), polyethylene glycol (PEG), or mixtures thereof.

17. The method of claim 16, wherein the subject performs the method.

18. The method of claim 16, wherein the method is completed in less than 60 minutes.

19. The detection system of claim 1, wherein the valve material comprises cotton, filter paper, cellulose, cellulose-derived materials, gel, polyurethane, polyester, rayon, nylon, microfiber, viscose, or alginate.

20. The detection system of claim 1, wherein the valve material comprises paper, and the dissolvable material comprises sucrose, trehalose, or a mixture thereof.

* * * * *